US012557812B2

(12) United States Patent
Rodensky et al.

(10) Patent No.: US 12,557,812 B2
(45) Date of Patent: Feb. 24, 2026

(54) METHOD AND COMPOSITION FOR WATER TREATMENT

(71) Applicants: BROMINE COMPOUNDS LTD., Beer-Sheva (IL); THE RESEARCH FOUNDATION FOR THE STATE UNIVERSITY OF NEW YORK, Binghamton, NY (US)

(72) Inventors: Michal Rodensky, Kfar Yedidya (IL); Chen Zolkov, Kiryat Tivon (IL); David G. Davies, Binghamton, NY (US)

(73) Assignees: BROMINE COMPOUNDS LTD, Beer-Sheva (IL); THE RESEARCH FOUNDATION FOR THE STATE UNIVERSITY OF NEW YORK, Binghamton, NY (US)

( * ) Notice: Subject to any disclaimer, the term of this patent is extended or adjusted under 35 U.S.C. 154(b) by 964 days.

(21) Appl. No.: 17/613,758

(22) PCT Filed: May 27, 2020

(86) PCT No.: PCT/IL2020/050591
§ 371 (c)(1),
(2) Date: Nov. 23, 2021

(87) PCT Pub. No.: WO2020/240559
PCT Pub. Date: Dec. 3, 2020

(65) Prior Publication Data
US 2022/0240503 A1 Aug. 4, 2022

Related U.S. Application Data

(60) Provisional application No. 62/853,205, filed on May 28, 2019.

(51) Int. Cl.
| | |
|---|---|
| *A01N 37/06* | (2006.01) |
| *A01N 33/20* | (2006.01) |
| *A01N 37/34* | (2006.01) |
| *A01N 59/00* | (2006.01) |
| *A61L 2/18* | (2006.01) |
| *C02F 1/76* | (2023.01) |
| *A61L 101/34* | (2006.01) |
| *A61L 101/36* | (2006.01) |
| *A61L 101/44* | (2006.01) |
| *C02F 103/02* | (2006.01) |

(52) U.S. Cl.
CPC ............. *A01N 37/06* (2013.01); *A01N 33/20* (2013.01); *A01N 37/34* (2013.01); *A01N 59/00* (2013.01); *A61L 2/18* (2013.01); *C02F 1/766* (2013.01); *A61L 2101/34* (2020.08); *A61L 2101/36* (2020.08); *A61L 2101/44* (2020.08); *C02F 2103/02* (2013.01); *C02F 2303/20* (2013.01)

(58) Field of Classification Search
None
See application file for complete search history.

(56) References Cited

U.S. PATENT DOCUMENTS

| | | | |
|---|---|---|---|
| 4,328,171 A | 5/1982 | Burk et al. | |
| 4,745,189 A | 5/1988 | Lee et al. | |
| 5,627,135 A | 5/1997 | Gartner | |
| 6,068,861 A | 5/2000 | Moore, Jr. et al. | |
| 7,524,884 B2 | 4/2009 | Lupin et al. | |
| 8,513,305 B2 * | 8/2013 | Davies ................... | A61P 31/00 562/598 |
| 8,748,486 B2 | 6/2014 | Wang et al. | |
| 2005/0061197 A1 * | 3/2005 | Nalepa .................. | A01N 43/50 106/15.05 |
| 2008/0317815 A1 | 12/2008 | Davies | |
| 2009/0178587 A9 | 7/2009 | Nalepa | |
| 2014/0093589 A1 * | 4/2014 | Feldman ............... | A01N 35/08 424/722 |
| 2019/0112207 A1 * | 4/2019 | Chapman ............... | A01N 25/30 |

FOREIGN PATENT DOCUMENTS

| | | |
|---|---|---|
| JP | 2015-150490 A | 8/2015 |
| KR | 2015-0135291 A | 12/2015 |
| WO | 1999/06320 A1 | 2/1999 |
| WO | 2003/031347 A1 | 4/2003 |
| WO | 2003/093171 A1 | 11/2003 |
| WO | 2008/143889 A1 | 11/2008 |
| WO | 2014/154946 A1 | 10/2014 |
| WO | 2019/079107 A1 | 4/2019 |

OTHER PUBLICATIONS

Sepehr, S., et al., PLoS ONE 9(7): e101677 (2014). (Year: 2014).*
Office Action issued for Japanese Patent Application No. 2021-570300 on Mar. 5, 2024, 6 pages.
International Search Report and Written Opinion issued for International Application No. PCT/IL2020/050591 on Jul. 21, 2020, 9 pages.
Davies, D.G. et al: "A Fatty Acid Messenger is Responsible for Inducing Dispersion in Microbial Biofilms"; Journal of Bacteriology, (Mar. 2009) vol. 191, No. 5, pp. 1393-1403.

* cited by examiner

Primary Examiner — David J Blanchard
Assistant Examiner — Daniel F Coughlin
(74) Attorney, Agent, or Firm — ROTHWELL, FIGG, ERNST & MANBECK, P.C.

(57) ABSTRACT

The invention provides a method of microbial control in water comprising adding to the water one or more bromine-based biocide(s) and cis-2-decenoic acid or a salt thereof. Compositions in the form of liquid concentrates comprising bromine-based biocides and cis-2-decenoic acid or a salt thereof are also described.

19 Claims, 13 Drawing Sheets

FIGURE 1

METHOD AND COMPOSITION FOR WATER TREATMENT

CROSS-REFERENCE TO RELATED APPLICATIONS

Figure 2A:
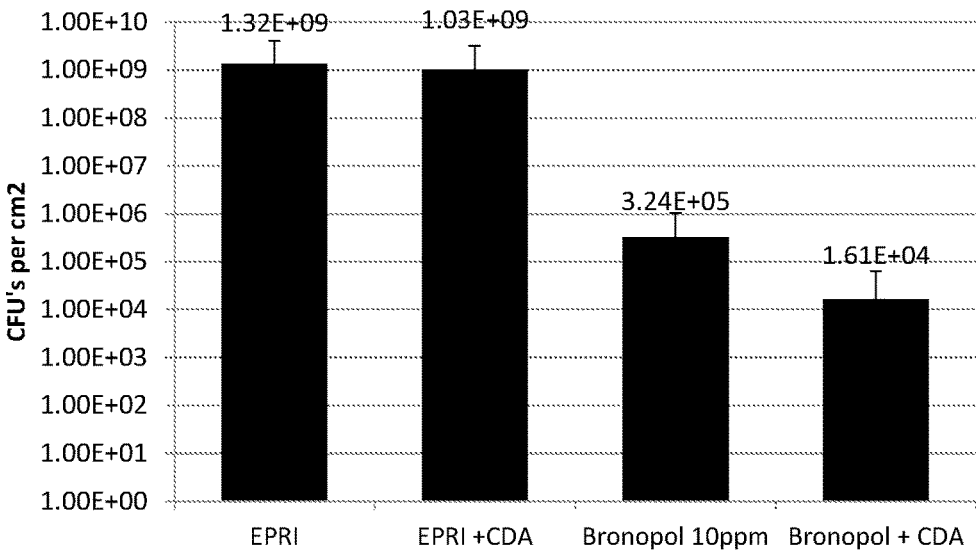

This application is a 35 U.S.C. 371 National Phase Entry Application from PCT/IL2020/050591 filed on May 27, 2020, which claims the benefit of the filing date of U.S. Provisional Application No. 62/853,205 filed on May 28, 2019, the entire contents of which are incorporated herein by reference.

The invention relates to microbial control of water, e.g., eliminating planktonic and biofilm bacteria using a bromine-based biocide in combination with an auxiliary agent which has been found to enhance the action of the biocide.

The use of bromine in industrial water treatment is well established and a variety of bromine-based biocides are currently available in the market. The working concentrations and frequency of supply of the biocide depend on the type of water, microbial load, organic load, the specific biocide under consideration, the dosing method, etc.

It has been reported by one of the present inventors [WO 2008/143889 and Journal of Bacteriology 191:1393-1403 (2009)] that cis-2-decenoic acid, produced by the bacterium *Pseudomonas aeruginosa*, is capable of inducing *P. aeruginosa* and other gram-negative and gram-positive bacteria and fungi to undergo a physiologically-mediated dispersion response, resulting in the dis-aggregation of surface-associated microbial populations and communities known as biofilms.

Control of biofilm constitutes an important aspect of water treatment programs. In US 2009/0178587, the performance of bromine-based biocides in controlling biofilms of *P. aeruginosa* was investigated. It has been also proposed in US 2009/0178587 to increase the efficiency of the treatment with the aid of surfactants that act as bio-dispersants, but no experimental data was given to illustrate this approach.

The present invention describes the use of cis-2-decenoic acid as an adjunctive to bromine-containing biocides in the treatment of biofilm and planktonic bacteria in water systems and on surfaces in contact with the water. Experimental work conducted in support of this invention in laboratory models indicates that the combination of cis-2-decenoic acid with acceptable working concentrations of a bromine-containing biocide, shows a significant enhancement in the killing of bacteria in both pure and mixed cultures typically found in industrial and natural waters relative to treatment with the biocides alone. Furthermore, the activity of cis-2-decenoic acid with the biocide compounds enhances the efficacy of brominated biocides, allowing for a reduction in the effective quantities of the biocides used.

It is also worth noting that while incorporation of cis-2-decenoic acid (CDA) into bromine-based water treatment greatly improves the effectiveness of biofilm control compared to the brominated biocide acting alone, a smaller effect is observed in chlorine-based water treatment. For example, it is shown below that under comparable conditions, the combined treatment bromine/CDA achieves biofilm bacteria count that is ~2.5 log units lower than that achieved by chlorine/CDA treatment.

The invention is therefore primarily directed to a method of microbial control in water, comprising adding to the water one or more bromine-based biocide(s) and cis-2-decenoic acid (or a salt thereof) to achieve, for example, reduction of planktonic and/or biofilm bacteria, algae and fungi on a surface in contact with the water.

CDA can be easily incorporated into bromine delivery systems that are currently employed in the treatment of industrial water. For example, the bromine-based biocide(s) and CDA can be delivered to an industrial water stream in contact with an infested surface using multiple feed solutions injected sequentially or simultaneously, either continuously or in batch mode to the water stream; the simultaneous injection may include the pre-mixing of the individual solutions to produce a single additive solution (i.e., the CDA and biocide solutions can be mixed before or just prior to addition to the water stream). The selected feeding method also depends on whether the biocide is supplied as a single component or not, as described below.

To enable water treatment using a single additive feed instead of multiple additives feeds, we prepared liquid concentrates comprising suitably proportioned combinations of bromine-based biocide and CDA, which exhibit good room temperature storage stability.

Accordingly, another aspect of the invention is a composition (e.g., a liquid concentrate) comprising one or more bromine-based biocides and cis-2-decenoic acid in a liquid carrier comprising water, water miscible solvent or mixture thereof, and optionally one or more additive(s) such as cosolvent(s), antifreeze(s) and stabilizer(s), e.g., antioxidants. Solid compositions comprising the biocide and CDA, e.g., granules, flakes & tablets, are also contemplated by the present invention.

Bromine-based biocides suitable for use in the present invention are available in the marketplace in different forms, i.e., solids (such as powders and compacted forms e.g., granules and tablets) and liquids (e.g., aqueous concentrates or other flowable formulations that can be easily supplied to the aqueous system to be treated). The bromine-based biocidal agents are commonly divided into two classes:

A) non-oxidizing biocides; and

B) oxidizing biocides.

Non-oxidizing biocides may be selected from the group of:

A1: 2-bromo-2-nitro-1,3-propanediol (bronopol); the synthesis of bronopol is described, for example, in WO 2009/107133. The product is available (e.g., from ICL-IP) in a powder form or an aqueous solution and its normal dose level as active ingredient lies in the range from 1 to 1000 ppm (when used alone, e.g., from 1 to 300 ppm).

A2: 2,2-dibromo-3-nitrilopropionamide; the synthesis of DBNPA is described, for example, in U.S. Pat. No. 4,328,171. Aqueous concentrates and compacted forms of DBNPA are described in U.S. Pat. Nos. 5,627,135 and 7,524,884, respectively. DBNPA is commercially available (e.g., from ICL-IP). When used alone, dose rates as active ingredient are in the range from 1 to 1000 ppm (e.g., 1-200 ppm).

A3: other examples of non-oxidizing bromine-based biocides that can be mentioned include 2-Bromo-4-hydroxyacetophenone (BHAP), bis-bromo acetyl butene (BBAB) and β-bromo-β-nitro-styrene (BNS).

Oxidizing bromine-based biocides are compounds which release active bromine species in water (e.g., hypobromous acid/hypobromite), either by dissolution/dissociation or through bromide oxidation that converts the Br⁻ to elemental bromine/Br⁺ (the oxidation is usually achieved with the aid of a chemical oxidant; however, supply of electrolytically-generated bromine to the water system to be treated is also included herein in conjunction with CDA). The dosage of the oxidative biocides described herein is usually expressed as total $Cl_2$ that can be determined by iodometric titration using a titroprocessor: Titrino 848 plus or by DPD (Diethyl-p-PhenyleneDiamine) reagent method using a SQ-300 spectrophotometer: Merck SQ-300. Oxidizing bromine-based biocides may be selected from the group of:

B1: N-brominated amides and imides, such as 1,3-dihalo-5,5-dialkylhydantoins, wherein at least one of the halogen atoms is bromine (the alkyl groups may be the same or different); commercially important biocides that belong to this class are 1-bromo-3-chloro-5,5-dimethylhydantoin (abbreviated BCDMH), 1-chloro-3-bromo-5,5-dimethylhydantoin, 1,3-dibromo-5,5-dimethylhydantoin (DBDMH) and also "mixed" alkyl compounds containing two different alkyl groups at position 5 of the ring, such as 1-bromo-3-chloro-methylethylhydantoin (BCMEH), 1-chloro-3-bromo-methylethylhydantoin or mixtures thereof. Methods of synthesizing 1,3-dihalo-5,5-dimethylhydantoins can be found, for example, in U.S. Pat. No. 4,745,189. The acceptable dose rate of 1,3-dihalo-5,5-dialkylhydantoins is 1 to 50 ppm as total $Cl_2$.

B2: inorganic bromide sources, namely bromide salts and hydrobromic acid, which release bromine species in water upon oxidation (e.g., by chemical oxidation using hypochlorite or chlorine gas and by electrochemical oxidation, namely, anodically-generated bromine). Commercially important products include activated sodium bromide (consisting of an aqueous solution of sodium bromide and sodium hypochlorite prepared on-site and delivered immediately to the water system to be treated); activated ammonium bromide (the biocide is prepared on-site by reacting ammonium bromide with an oxidizer); solution of HBr and urea (sometimes named herein bromourea) which reacts with sodium hypochlorite on-site (e.g., Bactebrom® solution, composed of HBr and urea, from ICL-IP); and dry mixtures of bromide/chlorine compound that are fed, for example, in a tablet form directly into the water system to be treated to react in-situ and produce the active bromine species. It should be noted that the abovementioned bromide sources such as sodium bromide, hydrobromic acid, ammonium bromide and the HBr (or NaBr) and urea solution may be oxidized on-site chemically (e.g., with hypochlorite or chlorine gas) or electrochemically.

B3: Other examples of oxidizing bromine-based biocides include sulfamate-stabilized bromine-based biocides, for example, as described in WO 99/06320 (stabilized aqueous alkali/alkaline earth metal hypobromite solution (e.g., with NaBr as bromide source)), or WO 03/093171; available from ICL-IP as Bromosol®. Bromine chloride and stabilized forms thereof (see U.S. Pat. No. 6,068,861) are available in the market as aqueous concentrates.

Turning now to cis-2-decenoic acid, it can be used as pure oil dissolved in a suitable solvent, such as ethanol. High purity CDA, e.g., 95% pure by gas chromatography (GC), is commercially available from various sources such as Carbosynth Ltd. (Compton-Berkshire, United Kingdom) and Chemodex (St. Gallen, Switzerland). However, the experimental work reported below indicates that satisfactory enhancement of bromine-based water treatments can be achieved with the aid of CDA of lower purity, say, 50%-95% pure oil by GC, e.g., 80-93%, for example, 89-91% (i.e., ~90%). The <95% (by gas chromatography, GC) pure CDA is named herein "low purity CDA grade". It may be appreciated that utilizing low purity CDA grade is economically advantageous. The term "pure CDA" refers to CDA characterized in having a purity level of more than 95%, e.g., equal to or greater than 97% as detected by GC.

CDA with any desired purity level can be obtained via the synthetic route described in U.S. Pat. No. 8,748,486, by halogenating 2-decanone $CH_3—(CH_2)_7—C(O)—CH_3$, to produce 1,3-dihalide ketones (e.g., reaction with elemental bromine to produce 1,3-dibromo-2-decanone), followed by dehalogenation in an alkaline environment generated by sodium or lithium hydroxide, to produce the terminal carboxylic acid group via the Favorski rearrangement and simultaneously the adjacent carbon-carbon double bond. The reaction mixture can then be worked-up by conventional techniques to recover CDA with purity levels suitable for use in the present invention, e.g. from 85 to 97% (by GC).

The combination bromine/CDA has proved surprisingly effective against biofilm in laboratory models across a broad concentration range of various bromine-based biocides. Biofilm-associated bacterial counts measured for the combined treatment are ~1-5 log units lower than for comparative values measured for the biocide acting alone. We use the term "enhancement" to indicate the difference in bacterial counts between treatments in which the biocide acts alone and in combination with CDA (CDA on its own does not reduce bacterial counts, as shown by the work reported below; notably, CDA alone failed to demonstrate biocidal action over a broad concentration range, even >3000 nM).

The performance of some selected bromine biocides, alone and in conjunction with different purity grades of CDA is tabulated in Table 1. The results show the effect of bromine/CDA on 3-day-old P. aeruginosa biofilm or biofilm formed by mixed bacteria, after short contact time: one hour contact time with CDA, followed by one hour contact time with the bromine-based biocide, at dosage levels of 310 nM and 5-20 ppm, respectively.

TABLE 1

| effect of sequential application of CDA and bromine biocide on 3-day-old *Pseudomonas aeruginosa* biofilm | | | |
|---|---|---|---|
| Biocide | Biocide dosage (ppm) | Log reduction vs. control: biocide alone | reduction Log control: vs. combination of the 310 nM CDA and biocide | Enhancement |
| DBNPA | 10 | ~3 | ~5 | ~2 |
| BCDMH | 10 | ~3.5 | ~6 | ~2.5 |
| Bromourea | 5 | ~2.5 | ~5-6 | ~2.5-3.5 |
| | 10 | ~2.5 | ~6-7 | ~4.5-5.5 |
| Activated NH₄Br | 5 | ~3 | ~7.5 | ~4.5 |
| BCDMH* | 10 | ~2 | ~7.5 | ~5.5 |
| Activated NaBr | 20 | ~5 | ~7 | ~2 |

*biofilm formed by mixed bacteria (three different bacterial: *Staphylococcus aureus* 6538, *Bacillus mycoides* 6462 and *Pseudomonas aeruginosa* 700888)

In another test reported below, the simultaneous application of one major non-oxidizing bromine biocide (bronopol) and CDA was proved effective in eradicating P. aeruginosa biofilm at the following treatment level: 10 ppm bronopol/310 nM CDA after contact time of twenty-four hours. The results are tabulated in Table 2.

5

TABLE 2

| Biocide | Biocide dosage (ppm) | Log reduction vs. control: biocide alone | Log reduction vs. control: combination of the 310 nm CDA and biocide | Enhance-ment |
|---------|---------------------|---------------------|---------------------|--------------|
| Bronopol * | 10 | ~6 | ~9 (eradication) | ~3 |
| BCDMH ** | 10 | ~4 | ~6 | ~2 | effect of simultaneous application of CDA and bromine biocide on 3-day old *Pseudomonas aeruginosa* biofilm \* 24 hours contact time
\*\* 2 hours contact time Another significant set of results reported below shows that addition of a small amount of CDA can offset an appreciable decrease of the dosage level of the bromine-based biocide, thereby expanding the workable concentration range of bromine-based biocides. For example, with the aid of CDA, one major oxidizing biocide (bromourea) achieves reasonable biofilm control at a dosage level as low as 2.5 ppm (when acting alone at this dosage level, the biocide fails to generate a useful effect). The enhancement induced by the added CDA is roughly 4 log units. The same biocide eradicated biofilm at a dosage level of 5 ppm with 310 nM CDA. The results are summarized in Table 3.

TABLE 3

| Biocide | Biocide dosage (ppm) | Log reduction vs. control: biocide alone | Log reduction vs. control: combination of the 310 nm CDA and biocide | Enhance-ment |
|---------|---------------------|---------------------|---------------------|--------------|
| bromourea | 2.5 | ~0.5 | ~4 | ~3.5 |
| | 5 | ~6 | ~(eradication) | ~2 | effect of sequential application of CDA and bromine biocide on 3-day-old *Pseudomonas aeruginosa* biofilm In view of the above, bromine-based water treatments could benefit from the addition of CDA in a number of ways:

1) Because cis-2-decenoic acid has been shown to be bioactive in the presence of bromine-containing biocides within the range of concentrations typically used to treat biofouling in water systems, CDA may be straightforwardly incorporated into bromine-based water treatment programs under the regular dosage levels and frequency of biocide dosing according to the program, i.e., without altering the rate of application of the biocide, to achieve improved biofilm control by periodically or continuously injecting the CDA into the water stream that comes in contact with the biofilm (prior to, simultaneously with, or subsequent to biocide delivery to the water), or on occasion, especially in response to an indication of formation of highly severe biofilm, to achieve rapid control.

Accordingly, another aspect of the invention is a method of microbial control in water, which comprises combatting biofilm bacteria on a surface in contact with the water and/or inhibiting biofilm formation on a surface prone to such formation, by adding to the water an effective microbiocidal amount of the bromine-based biocide(s) and an enhancement-inducing amount of the cis-2-decenoic acid to achieve enhancement of at least 2 log units in biofilm reduction compared with the same dosage of the biocide acting alone, for example, down to $<10^5$ CFU/cm$^2$, e.g., $<10^3$ CFU/cm$^2$ and preferably $<10^2$ CFU/cm$^2$ or even substantial biofilm eradication, i.e. $<10^1$ CFU/cm$^2$.

The effective microbiocidal amount of the bromine-based biocide(s) is from 0.1 to 1000, e.g., 0.1 to 300 ppm as active biocide, for example, 0.5 to 100 ppm, and the enhancement-inducing amount of CDA is from 1 nM to 30 mM. It should be borne in mind that dosage levels may vary broadly depending on factors such as the identity of biocide and intended use. But in general, effective dosing ratios biocide: CDA as w/w in the water stream may vary in the range from 20:1 to 5000:1 preferably from 100:1 to 3000:1. The enhancement-inducing amount of CDA can be determined by trial and error in the site of use to achieve targeted biofilm reduction.

For example, an enhancement-inducing amount of CDA could be from 0.001 to 5 ppm, e.g., from 0.005 to 5 ppm, for example, from 0.01 to 1 ppm. As shown below, good results were observed across 0.005 to 0.5 ppm range (corresponding to ~30 to 3000 nM CDA).

2) Because cis-2-decenoic acid offsets reduction in bromine-based biocide dosing, allowing smaller quantities of the biocides to be used in an effective manner and achieve biofilm control comparable to higher dose treatments, cis-2-decenoic acid can modify program treatment by reducing biocide dosage level and/or frequency of biocide dosing. For example, the water system may be tracked for residual bromine and once the residual bromine values decay below a predetermined threshold, CDA can be injected to support the maintenance of the system with the low residual bromine to inhibit biofilm formation. That is, to enhance the activity of residual biocide in a water sample any time over the period of time that an active biocide is present in a system.

Accordingly, another aspect of the invention is a method of industrial water treatment comprising supplying bromine to the water for combatting biofilm bacteria on a surface in contact with the water and/or inhibiting biofilm formation on a surface prone to such formation, wherein the rate of application of bromine is varied over the treatment, such that switching to a low dosing level of bromine is accompanied by CDA addition to the water stream.

The present invention is particularly directed to provide microbial control over *Pseudomonas aeruginosa, Staphylococcus aureus, Bacillus mycoides, Candida albicans, Aspergillus niger*, and combinations of microorganisms growing in mixed-species communities derived from an industrial or an environmental water source.

Figure 1:
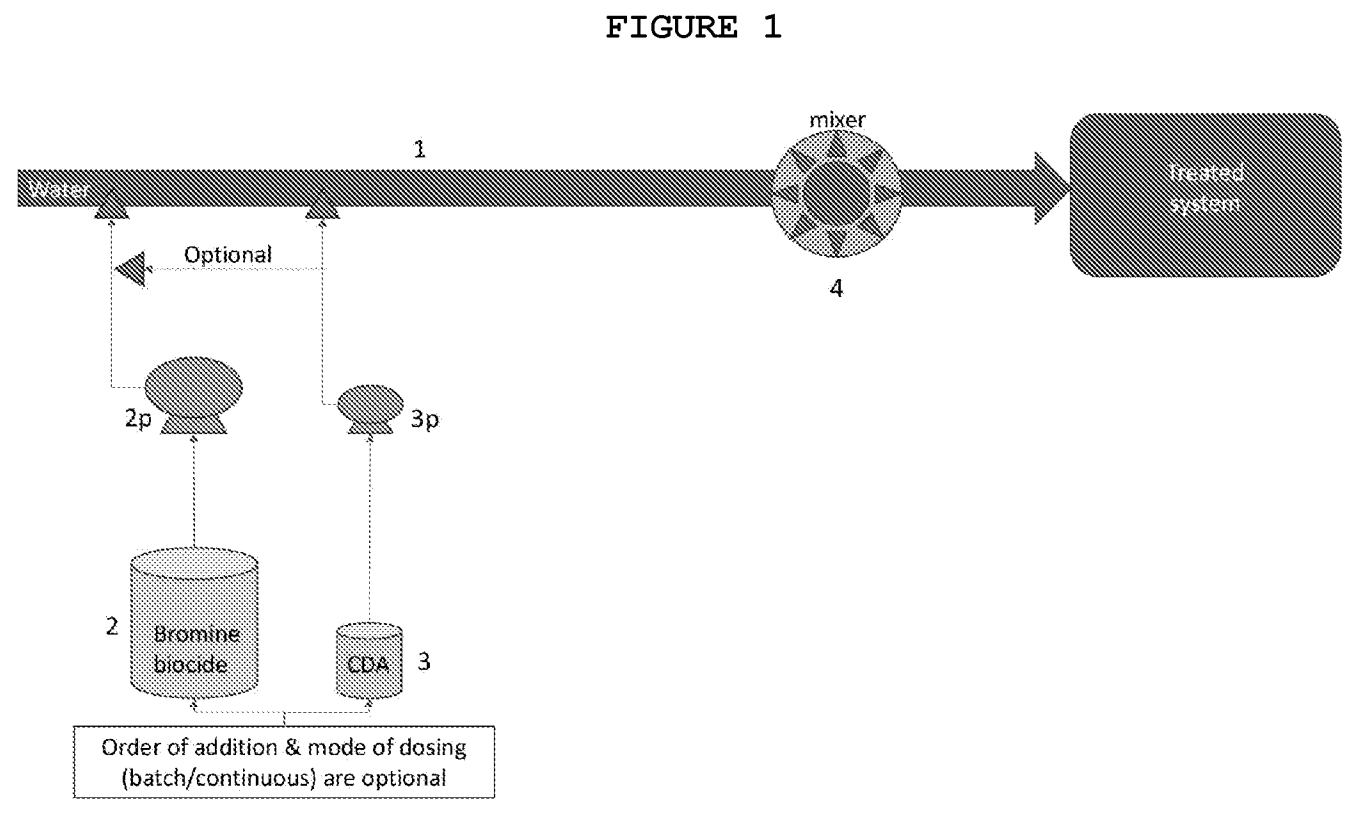

FIG. 1 schematically illustrates one convenient method to feed a bromine-based biocide and CDA into an industrial water system. The water stream that comes in contact with a biofilm surface or a surface prone to biofilm formation is indicated by numeral (1). We use the term "industrial water" to indicate any aquatic industrial water treatable by a bromine-based biocide, for example, recirculating and once-through cooling systems, cooling towers, pulp and paper mill systems, membranes, oil & gas applications, including biodiesel and diesel, floating production storage and off-loading (FPSO) systems, sulphate reduction units (SRU), steel mills, sugar & ethanol production, dairy production, swimming pools and spas, water distribution systems, irrigation systems, air washers, evaporative condensers, scrubbing systems, brewery pasteurizers, decorative fountains and oil recovery injection water.

It is seen that in the specific design illustrated in FIG. 1, the biocide and CDA are held separately in tanks (2) and (3), respectively, with their supply to the industrial water stream being accomplished by using two dosing pumps (2p and 3p). The design enables either sequential or simultaneous application of the two active components.

Biocides which fit well into the method shown in FIG. 1 are biocides which are applied as a single pumpable formulation, for example, non-oxidizing biocides available in the marketplace as storage stable liquid formulations, e.g., concentrated bronopol and DBNPA solutions (e.g., 5 to 50 wt % concentrates), and stabilized solutions of bromine or hypobromite (e.g., sulfamate-stabilized bromine-based biocide).

The design shown in FIG. 1 can be modified to enable the use of hypobromite-based biocidal solutions prepared on-site by oxidizing the bromide source just prior to use (these solutions must be applied immediately due to the instability of the hypobromite), by installing a third feed system into the process (i.e., one dosing pump is dedicated for supplying the CDA and two dosing pumps are used for the individual components of the biocide, i.e., the bromide source and the oxidant).

Incorporation of CDA into water treatments where the bromine based-biocide is applied in solid forms such as granules or tablets (fed to the inflow water line through erosion feeders) could be achieved by injecting the CDA solution with the aid of a dosing pump to the water line or to a subsidiary water stream diverted from the main stream into the feeder to dissolve the added solids.

The biocide and CDA solutions are dosed with metering pumps (2p and 3p, respectively) controlled by timers set up according to the treatment program. The biocide and CDA feed solutions may be injected directly to the water stream (1) but premixing of the two individual solutions in a mixing chamber (not shown) and delivery of the combined solution to the water stream is also possible to enable a treatment program based on simultaneous application of the two components of the treatment. To better control the treatment, monitoring and upstream mixing (4) devices are included, namely, halogen monitoring, oxidation reduction potential (ORP), pH sensors and online static mixers.

Regardless of the exact design, the separately supplied CDA can be applied neat or dissolved in a water miscible solvent or mixture of solvents such as aliphatic alcohols up to 4 carbons, tert-butyl methyl ether, tetrahydrofuran (THF), dimethyl sulfoxide (DMSO), glycols and polyethylene glycols, acetonitrile, optionally in the presence of surfactants and stabilizers.

In operation, sequential treatment with cis-2-decenoic acid can be performed by injecting the cis-2-decenoic acid from 20 minutes to 24 hours or more, prior to the biocide application. Cis-2-Decenoic acid may also be added following the biocide application to enhance the activity of the residual biocide in a water sample any time over the period of time that the active biocide is present in a system.

The method of the invention does not necessarily require multiple feeds as shown in FIG. 1. We have found that CDA is compatible with either the precursor of oxidative biocide (inorganic bromide sources), sulfamate-stabilized bromine-based biocides or with non-oxidizing biocides formulated in liquid concentrates, and that in the presence of suitable stabilizers, in particular an antioxidant (for example, butylated hydroxytoluene BHT), such liquid concentrates remain stable at room temperature over long storage periods against degradation of either the biocide or CDA. Accelerated tests also indicated acceptable stability. Such liquid concentrates can be dosed to the industrial water system using the proper feed system and are conveniently amenable to a simultaneous biocide/CDA treatment program. Accordingly, the invention also provides a method wherein the bromine-based biocide(s) and CDA are supplied to an industrial water stream in contact with an infested surface using a single feed solution, whereby the biocide and CDA are added simultaneously to the water. Thus, the invention relates to a composition comprising one or more bromine-based biocides and cis-2-decenoic acid or a salt thereof (e.g., for use in the method).

For example, a nonoxidizing bromine-based biocide and CDA are formulated in a liquid concentrate, which is supplied to the industrial water stream using a single feed solution.

The liquid concentrates of the present invention comprise:
a suitably proportioned mixture of (one or more) nonoxidizing bromine-based biocide(s) and cis-2-decenoic acid (or a salt thereof), e.g., at a weight ratio from 1000:1 to 50:1, preferably from 500:1 to 50:1, e.g., from 250:1 to 50:1, such that on dilution in an industrial water stream the two active components are applied at an effective ratio; for example, in the liquid concentrate, the concentration of the biocide is from 2 to 50%, preferably from 10 to 50% and the concentration of cis-2-decenoic acid is from 0.05 to 1%, preferably from 0.1 to 0.5% (by weight based on the total weight of the liquid concentrate); and a carrier comprising water, water miscible solvent or a mixture thereof (i.e., water alone, organic solvent alone or aqueous/organic solvent system); and optionally one or more of the following components: cosolvents (e.g., glycols in which the nonoxidizing bromine-based biocide exhibits high stability and solubility), antifreezes and stabilizers (e.g., an antioxidant).

One preferred room temperature storage stable liquid concentrate provided by the present invention comprises:
from 2.0 to 40.0% of 2-bromo-2-nitro-1,3-propanediol (e.g., from 10 to 35%);
from 0.05 to 0.5% of cis-2-decenoic acid (e.g., from 0.1 to 0.3%);
from 5.0 to 80.0% of water (e.g., from 10 to 30%);
from 10 to 70.0% of glycol such as ethylene glycol, propylene glycol, dipropylene glycol monomethylether;
from 0.05 to 0.5% of an antioxidant (e.g. butylated hydroxytoluene).

Another preferred room temperature storage stable liquid concentrate provided by the present invention comprises:
from 5.0 to 50.0% of 2,2-dibromo-3-nitrilopropionamide (e.g., from 15 to 25%);
from 0.05 to 0.5% of cis-2-decenoic acid (e.g., from 0.1 to 0.3%);
from 10 to 60.0% of water (e.g., from 10 to 20%);
from 40 to 60.0% of a glycol (such as polyethylene glycol with average molecular weight of 200);
from 0.05 to 0.5% of an antioxidant (e.g. butylated hydroxytoluene).

The concentrates are readily prepared by combining cis-2-decenoic acid (or a salt thereof), the nonoxidizing bromine-based biocide in a solid form, the glycol, water and the stabilizer under stirring at room temperature to obtain a clear solution.

EXAMPLES

Materials

Materials and reagents used in the experimental work are tabulated in Table 4.

TABLE 4

| Commercial name | Name of the biocide | Typical dosage* (ppm) | Source |
|---|---|---|---|
| C-103 | DBNPA | 0.1-1000 | Bromine compounds (ICL-IP) |
| Bromotop ® | Bronopol | 0.1-1000 | Bromine compounds (ICL-IP) |
| Bactebrom ® | Activated HBr:Urea mixture (Bromourea) | 0.1-100 | Bromine compounds (ICL-IP) active form prepared prior to use, as described in Preparation 1 |
| Halogene ® | BCDMH | 0.1-100 | Bromine compounds (ICL-IP) |
| Bromosol ® | Bromosulfamate | 0.1-100 | Bromine compounds (ICL-IP) |
| Bromide plus | Activated NaBr (NaOBr) | 0.1-100 | Bromine compounds (ICL-IP); Active form prepared prior to use |
| Ammonium Bromide | Activated AmBr | 0.1-100 | Bromine compounds (ICL-IP); active form prepared prior to use, as described in Preparation 2 |
| HBr 48% | | | Bromine compounds (ICL-IP) |
| Sodium hypochlorite 10-12% | Sodium hypochlorite | 0.1-100 | F&C Israel |
| Cis Decenoic acid ~97% pure (GC) | CDA pure | | Carbosynth Ltd. (Compton - Berkshire, United Kingdom) Chemodex (St. Gallen, Switzerland) |
| Cis Decenoic acid ~90% pure (GC) | CDA crude | | as described in preparation 3 |

*As active biocide

Methods

GC measurement was done with AGILENT HP-5 19091J-413 30 m*0.32 mm*0.25 micron.

Method: 50° C.//2'//10° C./min//280° C.//5° C./min//300° C./2'.

Preparation 1

Biocide Preparation by Activation of HBr/Urea Solution

Stock solution 1—8.94 g of Bactebrom® from ICL-IP (HBr:urea solution) diluted with 241.06 g of distilled water.

Stock solution 2—NaOCl ~1% prepared by 23.58 g of NaOCl 10.6% w/w diluted with 226.42 g of distilled-water.

Stock solution 2 (250.00 g of NaOCl 1.0%) was added gradually while stirring to the above diluted Bactebrom® solution (stock solution 1), to get the active biocide (orange solution)—total weight 500.00 g. Expected biocide concentration as determined by iodometric titration using Titroprocessor: Titrino 848 plus: ~0.5% as $Cl_2$ (~5000 ppm as $Cl_2$). The desired biocide concentration in each experiment was obtained by dilution with distilled water.

Preparation 2

Biocide Preparation by Activation of Ammonium Bromide

975 µl 10.25 Wt % aq. NaOCl was diluted with distilled water to 100 ml in a volumetric flask. $Cl_2$ concentration was ~1000 ppm as $Cl_2$ as determined by iodometric titration using Titroprocessor: Titrino 848 plus.

213 mg $NH_4Br$ was diluted with distilled water to 100 ml in a volumetric flask.

Mix equal volumes of 5 ml as follows: add the NaOCl solution in one stroke to a mixed solution (using a magnetic stirrer) of the $NH_4Br$ solution at ambient temperature.

The concentration of the product (activated AmBr) was based on the concentration of the Na-Hypochlorite (~1000 ppm as $Cl_2$). Equal volumes of the reactants were mixed to obtain the concentration of the active chlorine in the mixture as 50% of the concentration of the reactant NaOCl, ~500 ppm as $Cl_2$. The desired biocide concentration in each experiment was obtained by dilution with distilled water.

Preparation 3

Synthesis and Purification of Cis-2-Decenoic Acid

Cis-2-decenoic acid was prepared according to the two-step synthetic pathway described in U.S. Pat. No. 8,748,486, replacing sodium hydroxide with lithium hydroxide in the second step (dehalogenation/rearrangement of 1,3-dibromo-2-decanone) as depicted below:

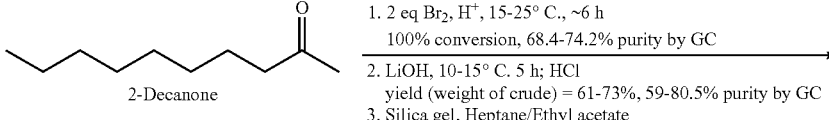

2-Decanone 1. 2 eq $Br_2$, $H^+$, 15-25° C., ~6 h
   100% conversion, 68.4-74.2% purity by GC
2. LiOH, 10-15° C. 5 h; HCl
   yield (weight of crude) = 61-73%, 59-80.5% purity by GC
3. Silica gel, Heptane/Ethyl acetate -continued

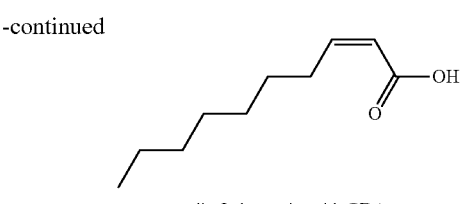

dis-2-decenoic acid, CDA

The reaction mixture was worked-up using conventional techniques (such as silica gel and solvent extraction) to recover cis-2-decenoic acid with purity varying in the range from 60 to 97% (GC). In the studies reported below, 90% pure cis-2-decenoic acid was tested.

Example 1

Enhancing the Effect of Bromine-Based Biocide on 3-Day Biofilm with the Aid of CDA (Simultaneous Application)

The effect of bromine-containing biocide in combination with CDA on pre-grown biofilms was studied. The experiment was carried out utilizing (A) the *P. aeruginosa* strain PA14 and (B) mixed bacterial species derived from environmental and industrial water.

Three bromine-based biocides were tested in this study: bronopol, DBNPA and BCDMH.

Experimental Procedure

Bacteria were cultured in EPRI medium supplemented with Hutners mineral solution and glucose (0.2%). Microorganisms were incubated at room temperature (22° C.), under aerobic conditions with shaking. The biofilm culture system used included polystyrene 24-well plates that were treated with protein to enhance attachment and growth of biofilm bacteria according to the method described in Davies D G, Marques C N, 2009, J Bacteriol 191:1393-1403.

Following inoculation with 1 mL bacterial culture, spent medium was removed and replaced with sterile medium every 24 hours for 3 days, and a final medium exchange was performed 3 hours prior to treatment. Additionally, the medium was exchanged prior to treatment in order to remove planktonic bacteria. Treatments consisted of 100 μL of 310 nM CDA and bromine-containing biocide, or bromine-containing biocide alone at concentrations used in commercial water treatment, water was used as a carrier, for a contact time determined by activity of each biocide and ranging from 1 hour to 24 hours, as detailed below for each of the tested biocides.

Following the treatment, the medium from each well was removed by pipet and 1 mL of DE neutralization broth was added in order to stop the treatment. Bacteria from each well were then removed by scraping the biofilm formed in the well with a sterile cell-scraper, and 1.0 mL of culture was transferred to chilled (4° C.) 9.0 mL DE neutralizing broth and homogenized for 15 seconds at 40,000 rpm on ice. Further dilutions were performed prior to enumeration (further neutralizing biocide activity). Recovery of bacteria were tested at different dilutions of biocide in water, in LB medium with thioglycolate and in DE neutralizing broth to ensure the active agent was properly neutralized. Viable bacteria were enumerated via the drop plate method. Each biocide was evaluated using 24-well plates with 8 wells each for the control cultures (Ctl) inoculated with *P. aeruginosa* but not treated, a CDA minus test (−CDA) treated with bromine-containing biocide only, and a CDA plus test treated with bromine-containing biocide and CDA (+CDA).

Figure 2B:
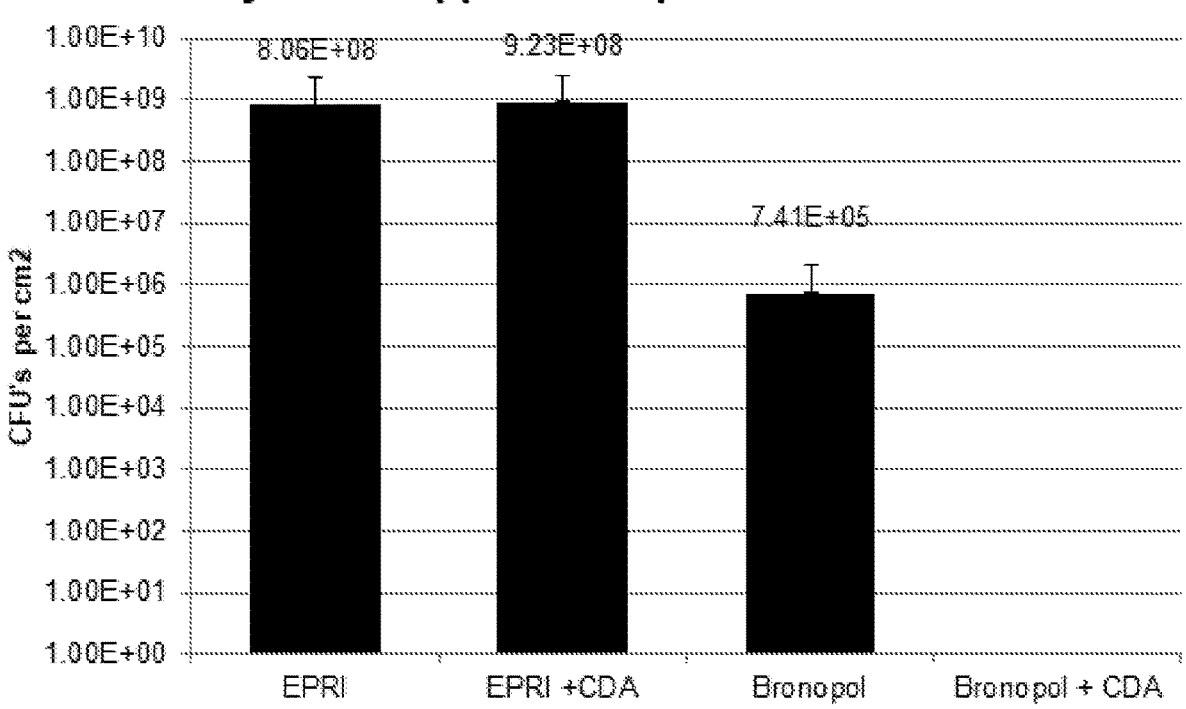

Results:

A) The results of the treatment of PA14 bacteria with 10 ppm of bronopol are presented in FIGS. 2A and 2B. FIG. 2A shows that the addition of CDA to the treatment with bronopol reduced the number of bacteria by more than an order of magnitude after only two hours of treatment. FIG. 2B demonstrates the effect achieved after 24 hours of treatment. It is seen that bronopol alone is very effective in reducing biofilm. Nevertheless, with the aid of added CDA, the treatment became much more effective and led to biofilm eradication.

Figure 3:
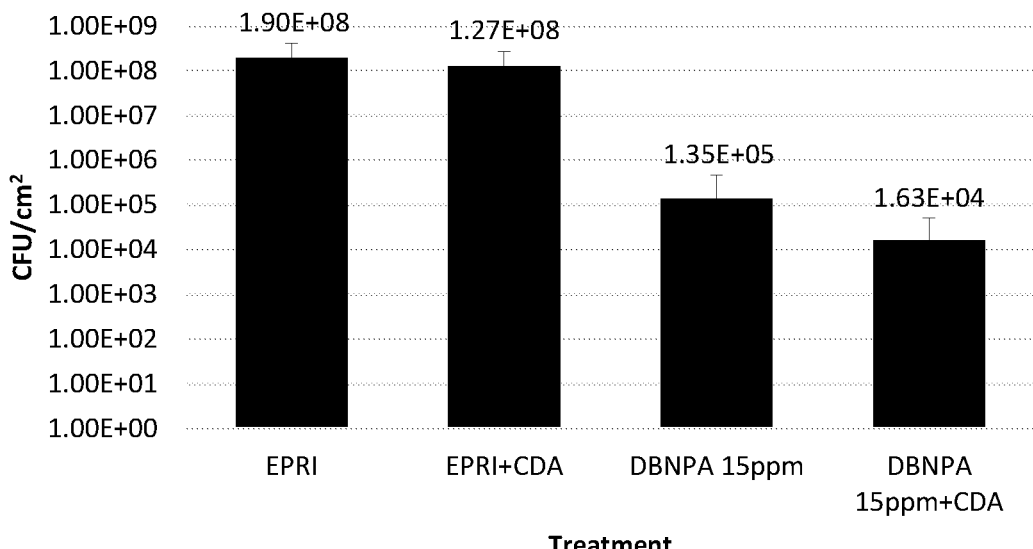

B. The results of the treatment of PA14 bacteria with 15 ppm of DBNPA are presented in FIG. 3 in the form of a bar diagram. It is seen that a short treatment of two hours which included both DBNPA and CDA yielded an improved effect compared with a treatment which was carried under the same conditions with DBNPA alone.

Figure 4:
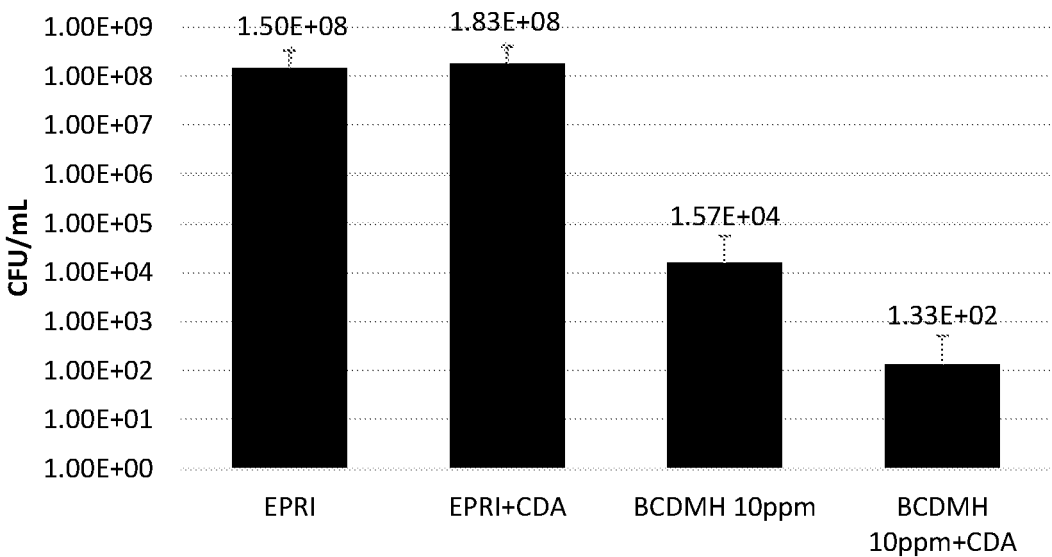

C. The results of the treatment of PA14 bacteria with 10 ppm of BCDMH are presented in FIG. 4 in the form of a bar diagram. It is seen that a short treatment of just one hour, which included the application of both BCDMH and CDA, generated an improved result compared with treatment using BCDMH alone (log reduction=2).

Figure 5A:
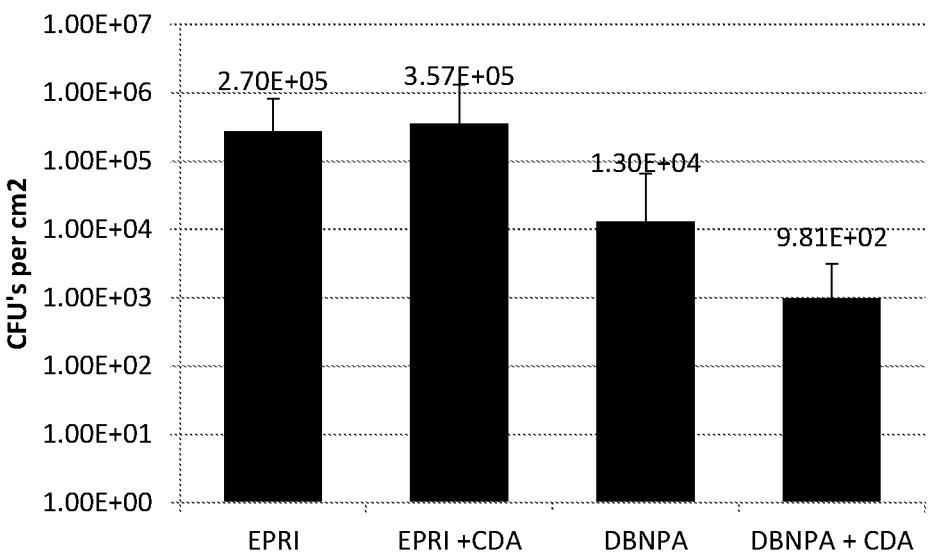
Figure 5B:
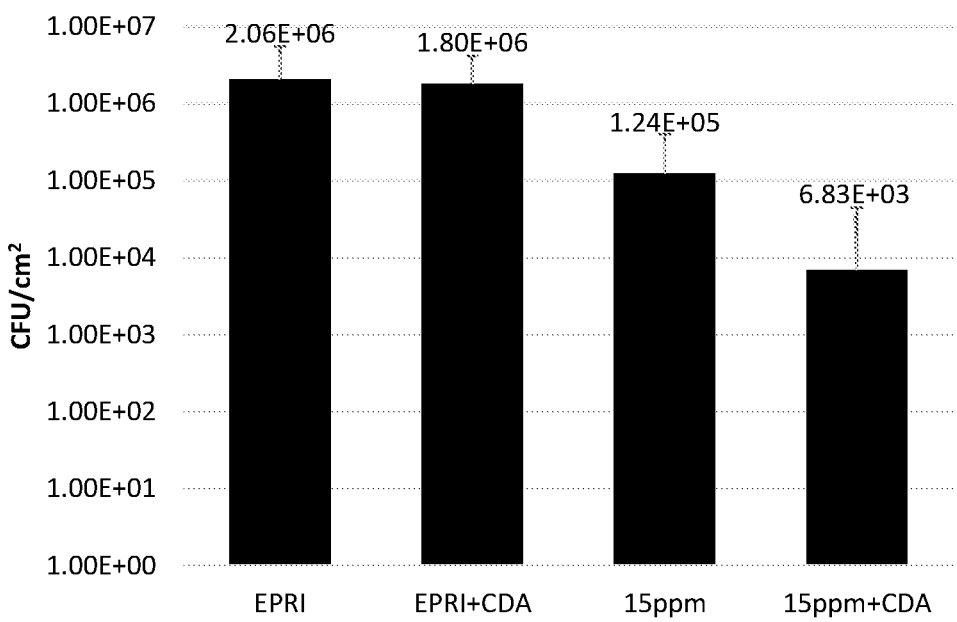

D. The results of the treatment against undefined mixed microbial biofilm cultures derived from an environmental water source and against a biofilm culture derived from fresh-water mixed microbial community that were obtained from cooling tower water, with 15 ppm of DBNPA are presented in FIGS. 5A and 5B respectively. It is seen that a short treatment of two hours which included both DBNPA and CDA yielded an improved result, compared with a treatment which was carried out under the same conditions with DBNPA alone.

Example 2

Enhancing the Effect of Bromine-Based Biocide on 3-Day Biofilm with the Aid of CDA (Sequential Application)

The effect of the sequential addition of CDA and bromine-containing biocide was studied using *P. aeruginosa* biofilm grown in the CDC biofilm reactor on borosilicate glass coupons (test method E2562). The addition of the bromine-containing biocide took place 60 min after the addition of 310 nM CDA. See Sections A-F, corresponding to six bromine-based biocides that were tested. In section G herein below, two more bacteria strains (*Staphylococcus aureus* 6538, *Bacillus mycoides* 6462) were added to the reactor and contributed to the formation of a mixed biofilm. In section H herein below, two other CDA concentrations (31 nM and 3100 nM) were tested against *P. aeruginosa* biofilm.

Six bromine-based biocides were tested (DBNPA, sulfamate-stabilized bromine, BCDMH, bromourea, activated ammonium bromide and activated NaBr) in combination with two CDA products of different purity: commercial CDA (CV-CHEM, 97% by GC) and crude CDA (90% by GC) of Preparation 3, to evaluate the effect of the purity level of the CDA used.

Experimental Procedure

The efficacy test on the coupons was performed according to the single tube method (E2871-13). This test method is used for growing a reproducible *P. aeruginosa* biofilm in a CDC Biofilm Reactor.

Biofilm Formation:

The biofilm was established by operating the reactor in batch mode (no flow of the nutrients) for 4 h. A steady state population was reached after the reactor operated for an additional 3 days with continuous flow of the nutrients. During the entire 3-day period, the biofilm was exposed to continuous fluid shear from the rotation of a baffled stir bar. At the end of the 3 days, the biofilm from the coupons was sampled as follows:

a. The coupons were rinsed to remove planktonic cells. The rods were oriented in a vertical position directly over a 50 mL conical centrifuge tube that contained 30 mL sterile buffered water. The rods were immersed with a continuous motion into the buffered water with minimal to no splashing, then immediately removed. A new 50 mL conical tube containing 30 mL sterile buffered water was used for each rod.

b. The rods were held with one of the randomly selected coupons centered over an empty, sterile 50 mL conical tube. The set screws were loosened, allowing the coupons to drop directly to the bottom of the tube.

Sequential addition of CDA and bromine-containing biocide:

a. Four mL of a solution containing either phosphate buffer (untreated control), a buffer with 310 nM CDA or a buffer with different concentrations of biocides were slowly pipetted into the tubes containing the coupons.

b. Each tube was tapped to release any air bubbles trapped below the coupon.

c. The tubes (containing the control, CDA or the biocide) were incubated at 20° C., under shaking at 200 rpm for one hour contact time.

d. After one hour contact time, 36 ml of a neutralizer was added to each tube.

e. The combined treatment was carried out as a sequential treatment in which CDA was introduced first, and after 1 hour contact time with CDA, the coupons were transferred to another tube containing the biocide and incubated at 20° C., under shaking of 200 rpm for another 1 hour contact time. After the one hour contact time, 36 ml of a neutralizer was added to each tube.

Removing and Disaggregating the Biofilm:

a. Each tube was vortexed using Vortex Genie-2 Model no. G560E on the highest setting for 30 s.

b. The tubes were sonicated at 45 kHz for 30 s.

c. The tubes were vortexed as described above, then sonicated and vortexed again.

d. The samples were serially diluted in buffered water.

e. Each dilution was cultured in duplicate (on R2A agar) for colony growth using the pour plating method.

f. The plates were incubated at 35° C. for 72 h.

g. The appropriate number of colonies were counted.

Figure 6:
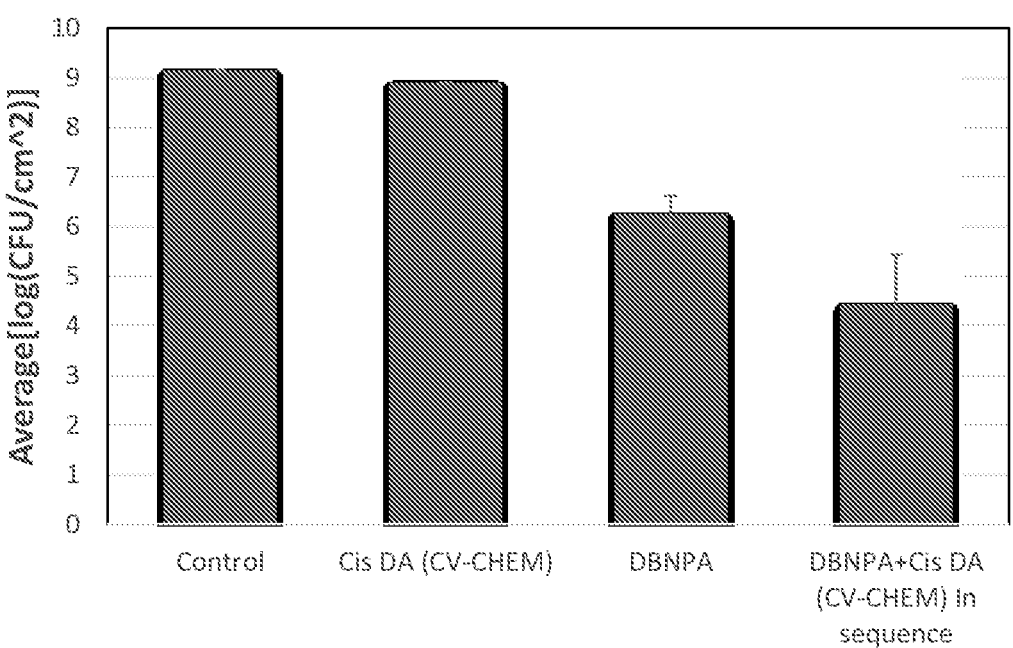

Results:

A. The effect of 10 ppm DBNPA (2,2-dibromo-3-nitrilopropionamide) on biofilms produced as described above, alone and in combination with 310 nM commercial CDA (CV-CHEM, 97% by GC) is illustrated in the bar diagram of FIG. 6. It is seen that CDA alone exhibits no useful effect compared to the control. The application of DPNPA alone reduces the biofilm. Notably, an enhancement of two log units was achieved by the combined treatment compared to the treatment with DBNPA alone (the combined treatment consists of addition of DBNPA to a sample that was in contact with CDA for one hour prior to the addition of the biocide).

Figure 7:
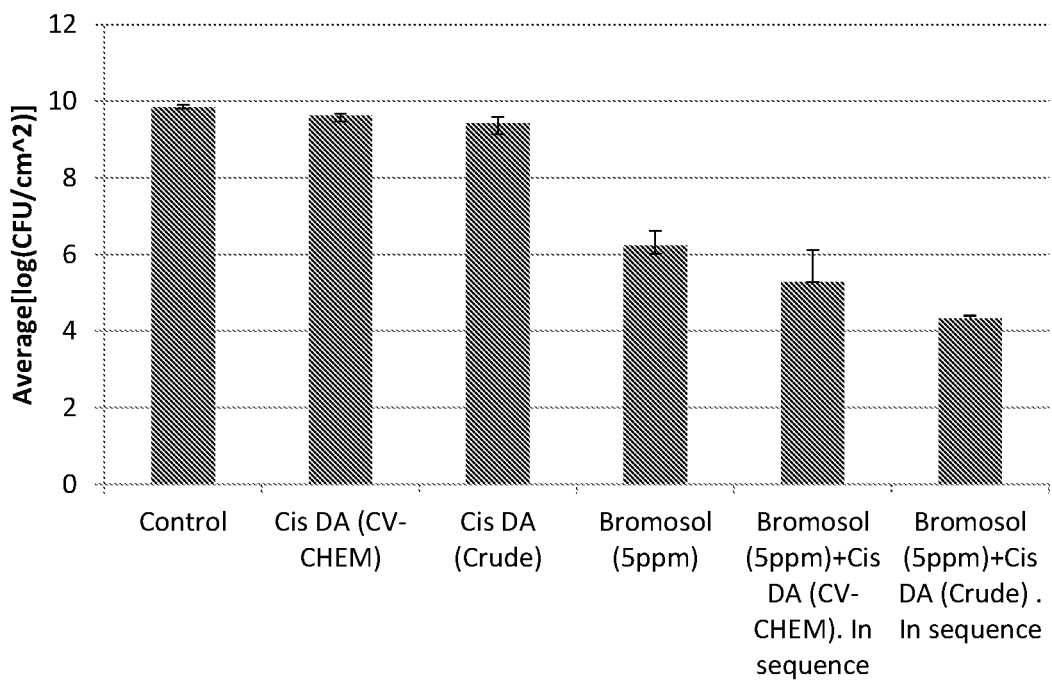

B. The effect of 5 ppm sulfamate-stabilized bromine (Bromosol) on biofilms produced as described above, alone and in combination with 310 nM CDA (either of commercial source from CV-CHEM, 97% by GC or of Preparation 3, 90% by GC) is illustrated in the bar diagram of FIG. 7. It is seen that CDA alone exhibits no useful effect compared to the control, regardless of its source. The application of Bromosol alone reduces the biofilm (4 log units). The combined treatment (that is, CDA followed by the biocide) achieves a further biofilm reduction compared to the treatment with the biocide alone. It is worth noting that the use of commercial and crude CDA has led to 1 log unit and 2 log unit reduction, respectively, relative to the biocide alone.

Figure 8:
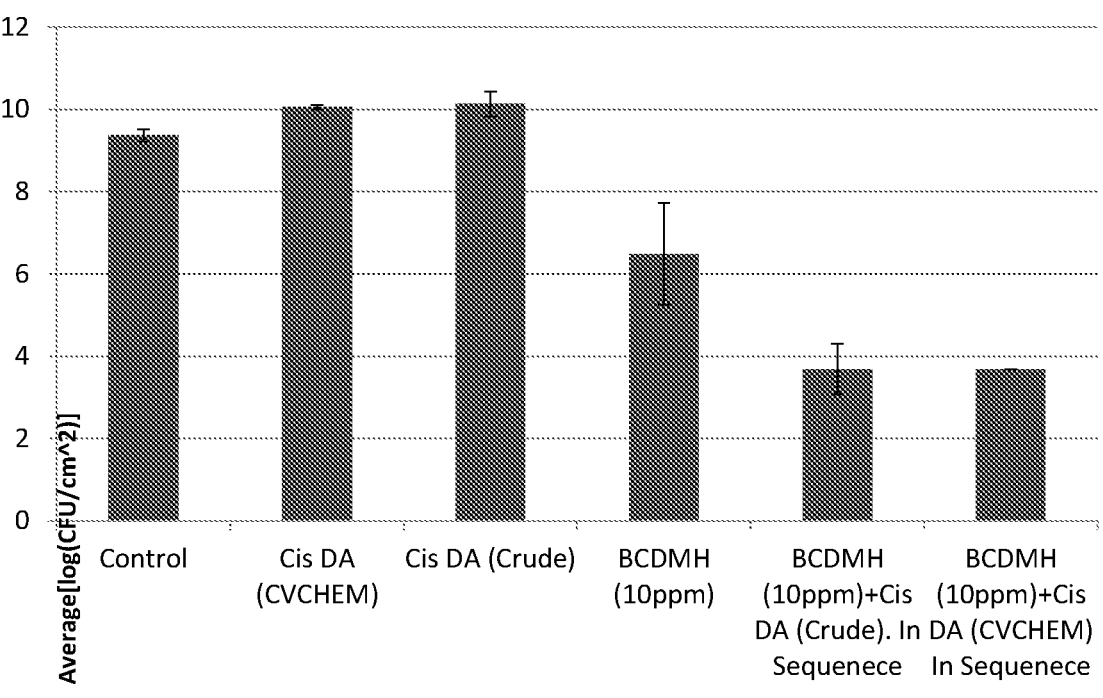

C. The effect of 10 ppm BCDMH on biofilms produced as described above, alone and in combination with 310 nM CDA (either of commercial source from CV-CHEM, 97% by GC or of Preparation 3, 90% by GC) is illustrated in the bar diagram of FIG. 8. It is seen that CDA alone exhibits no useful effect compared to the control, regardless of its source. The application of BCDMH alone reduces the biofilm (~3 log units). The combined treatment (that is, CDA followed by the biocide) achieves a further biofilm reduction compared to the treatment with the biocide alone; both commercial and crude CDA generated comparable enhancement, i.e., ~2 log units reduction relative to BCDMH alone.

Figure 9A:
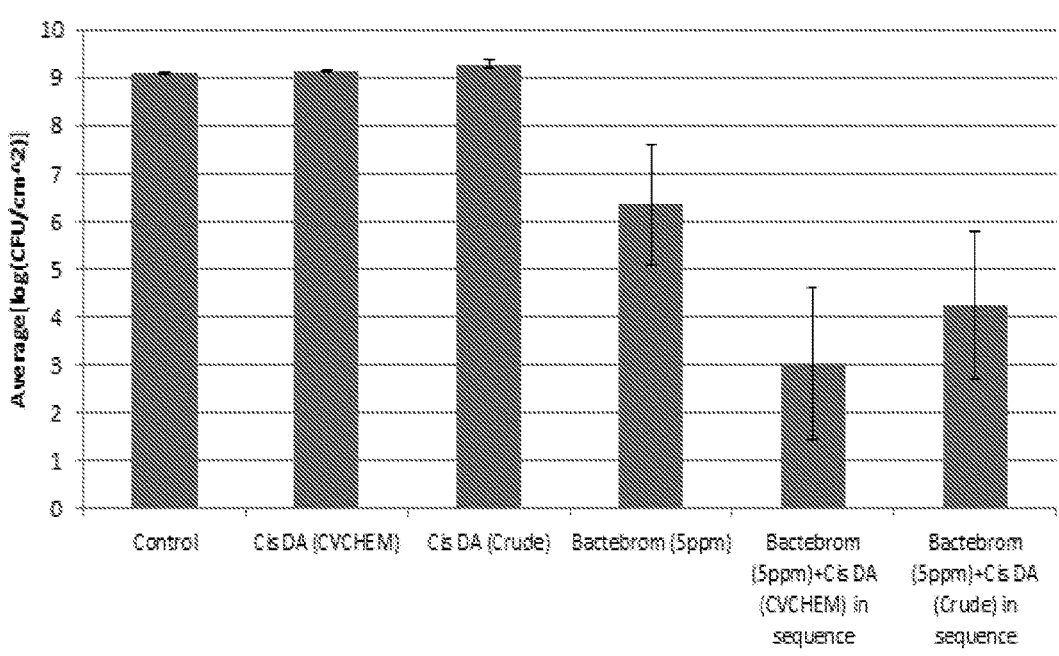
Figure 9B:
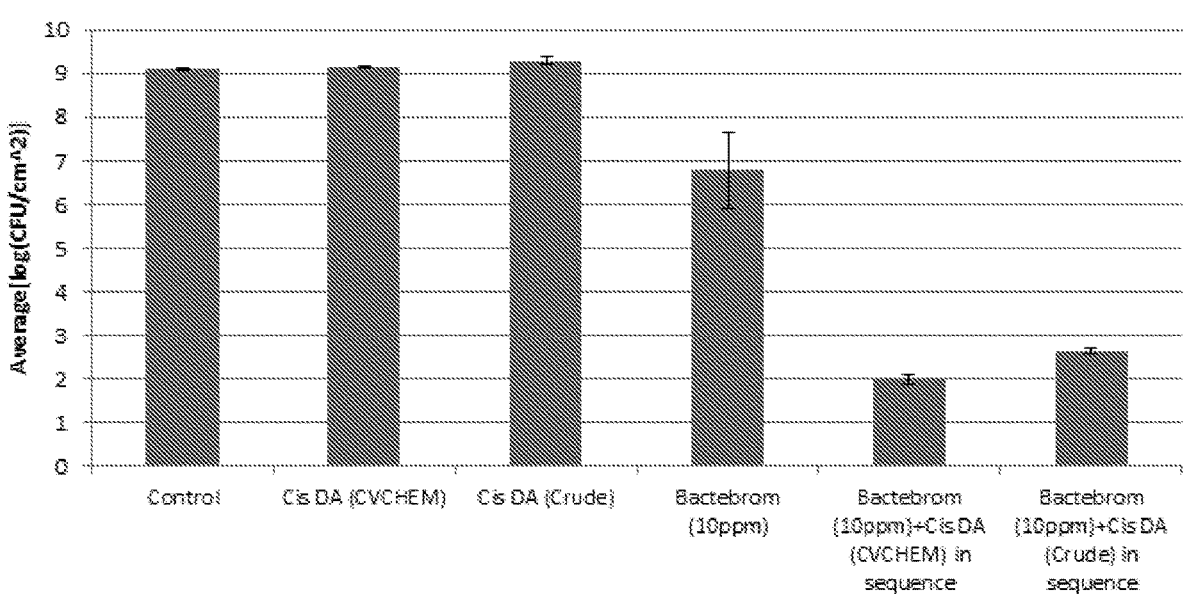

D. The effects of 5 ppm bromourea or 10 ppm bromourea on biofilms produced as described above, alone and in combination with 310 nM CDA (either of commercial source from CV-CHEM, 97% by GC, or of Preparation 3, 90% by GC) are illustrated in the bar diagrams of FIGS. 9A (5 ppm bromourea) and 9B (10 ppm bromourea). It is seen that CDA alone exhibits no useful effect compared to the control, regardless of its source. It is also worth mentioning that comparable biofilm reductions were measured for the solely applied 5 ppm bromourea and 10 ppm bromourea. That is, twofold increase of the concentration of the biocide (5 ppm→10 ppm) did not manifest itself in enhanced biofilm control. However, the combined treatment (application of CDA followed by application of 5 ppm biocide or 10 ppm biocide) achieves significant improvement compared to the treatment with the biocide alone; both commercial and crude CDA generated very good results i.e., ~2-3 log units enhancement relative to 5 ppm bromourea alone, and 4-5 log units enhancement relative to 10 ppm bromourea alone.

Figure 10:
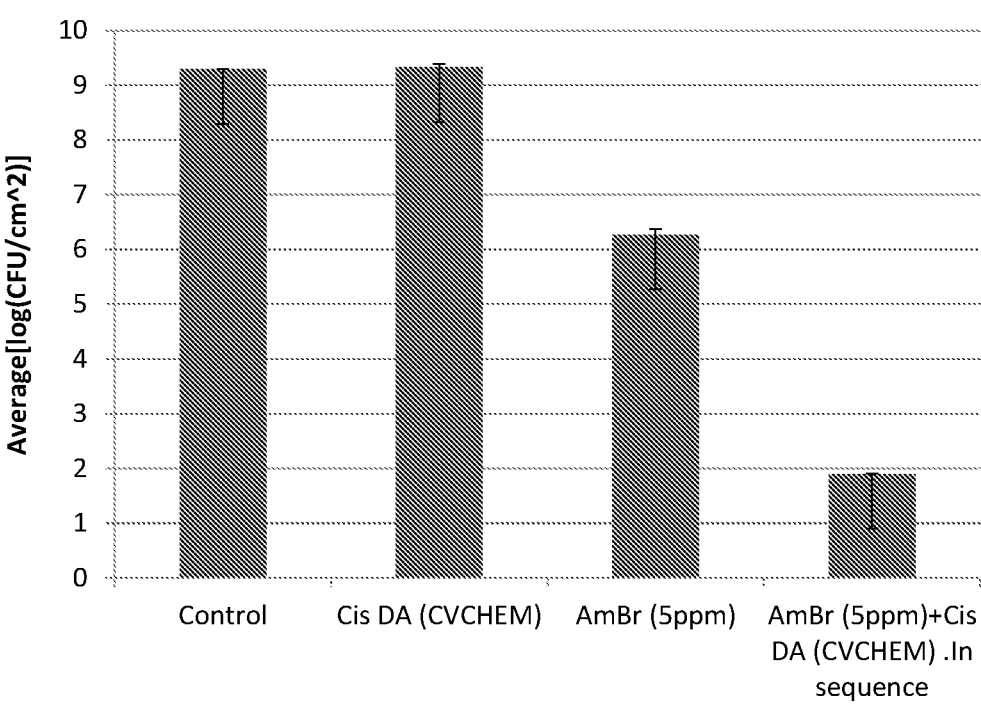

E. The effect of 5 ppm activated ammonium bromide (AmBr) on biofilms produced as described above, alone and in combination with 310 nM commercial CDA (CV-CHEM, 97% by GC) is illustrated in the bar diagram of FIG. 10. It is seen that CDA alone exhibits no useful effect compared to the control. The application of the biocide alone reduces the biofilm. Notably, an enhancement of ~4.5 log units was achieved by the combined treatment compared to the treatment with the biocide alone (the combined treatment consists of addition of the biocide to a sample that was in contact with CDA for one hour prior to the addition of the biocide).

Figure 11:
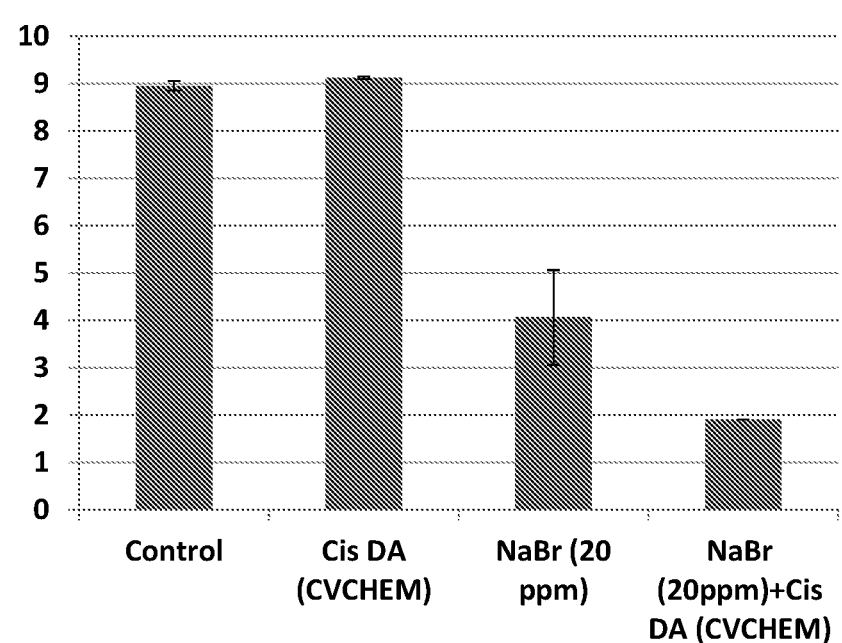

F. The effect of 20 ppm activated NaBr on biofilms, alone and in combination with 310 nM commercial CDA (CV-CHEM, 97% by GC) is illustrated in the bar diagram of FIG. 11. It is seen that CDA alone exhibits no useful effect compared to the control. The application of activated NaBr alone reduces the biofilm. Notably, an enhancement of two log units was achieved by the combined treatment compared to the treatment with activated NaBr alone (the combined treatment consists of addition of activated NaBr to a sample that was in contact with CDA for one hour prior to the addition of the biocide).

Figure 12A:
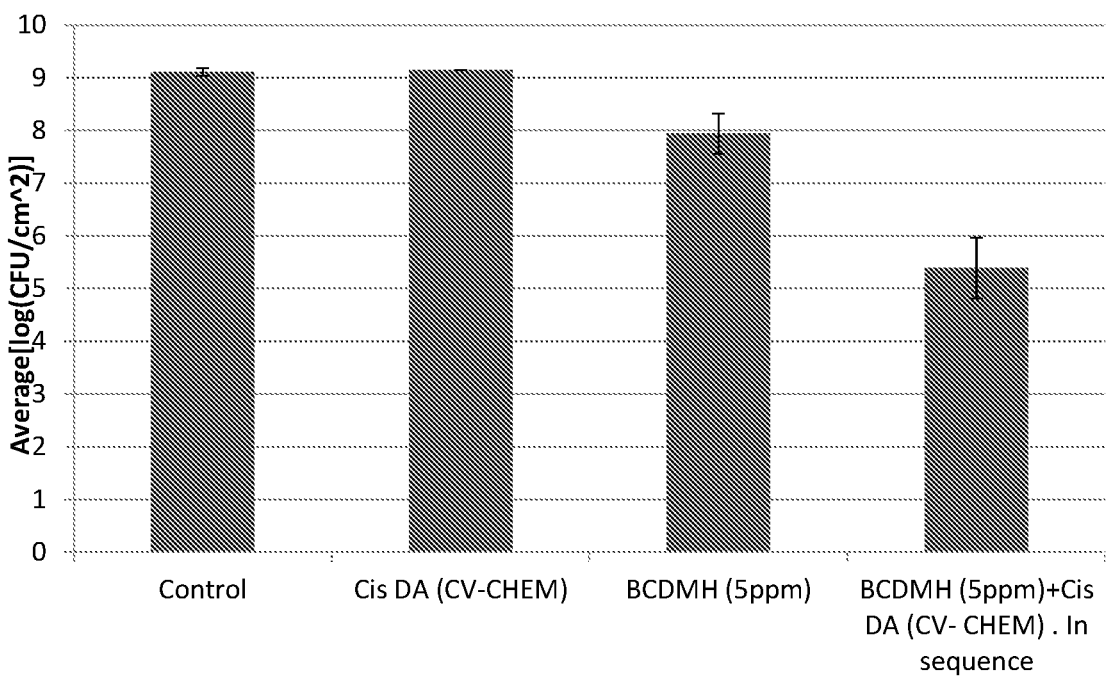
Figure 12B:
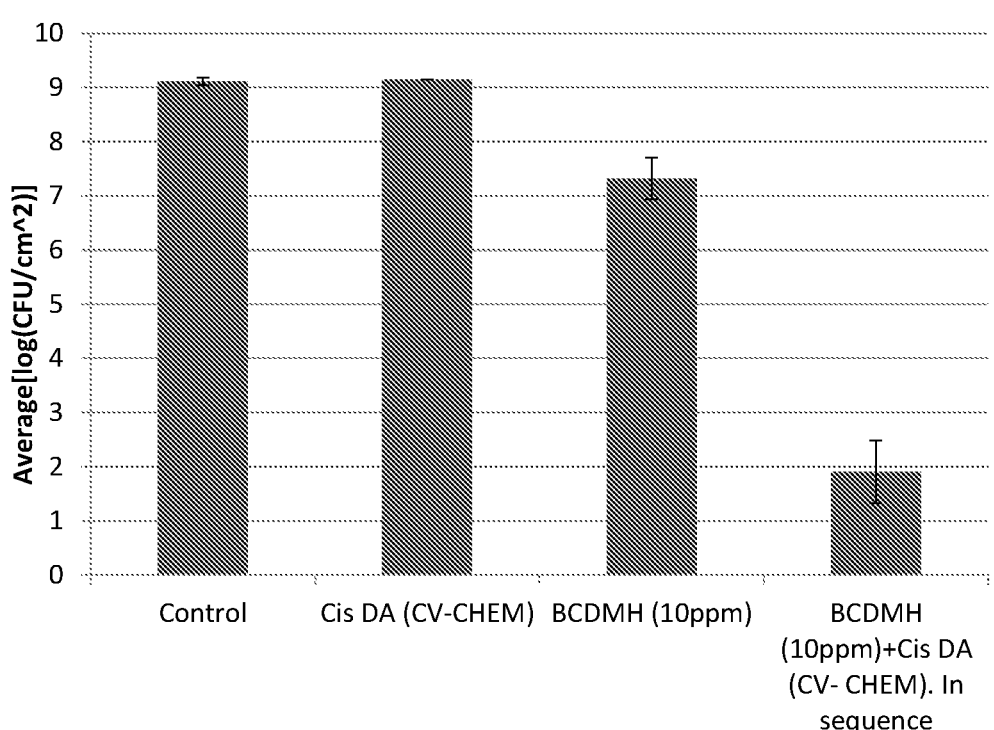

G. The effects of either 5 ppm BCDMH or 10 ppm BCDMH on a biofilm formed by mixed bacteria (three different bacteria: *S. aureus* 6538, *B. mycoides* 6462 and *P. aeruginosa* 700888) produced as described above, alone and in combination with 310 nM commercial CDA (CV-CHEM, 97% by GC) are illustrated in the bar diagrams of FIGS. 12A and 12B (5 ppm BCDMH or 10 ppm BCDMH, respectively). It is seen that CDA alone exhibits no useful effect compared to the control. The application of the biocide alone reduces the biofilm, but the 10 ppm BCDMH treatment is not appreciably better than the 5 ppm BCDMH treatment. However, both the 5 ppm and 10 ppm BCDMH treatments benefit from the incorporation of CDA into the treatment. The combined treatment has been found to achieve enhancement of ~2.5 and ~5.5 log units compared to the treatment with the 5 ppm and 10 ppm biocide acting alone, respectively (the combined treatment consists of addition of the biocide to a sample that was in contact with CDA for one hour prior to the addition of the biocide).

Figure 13:
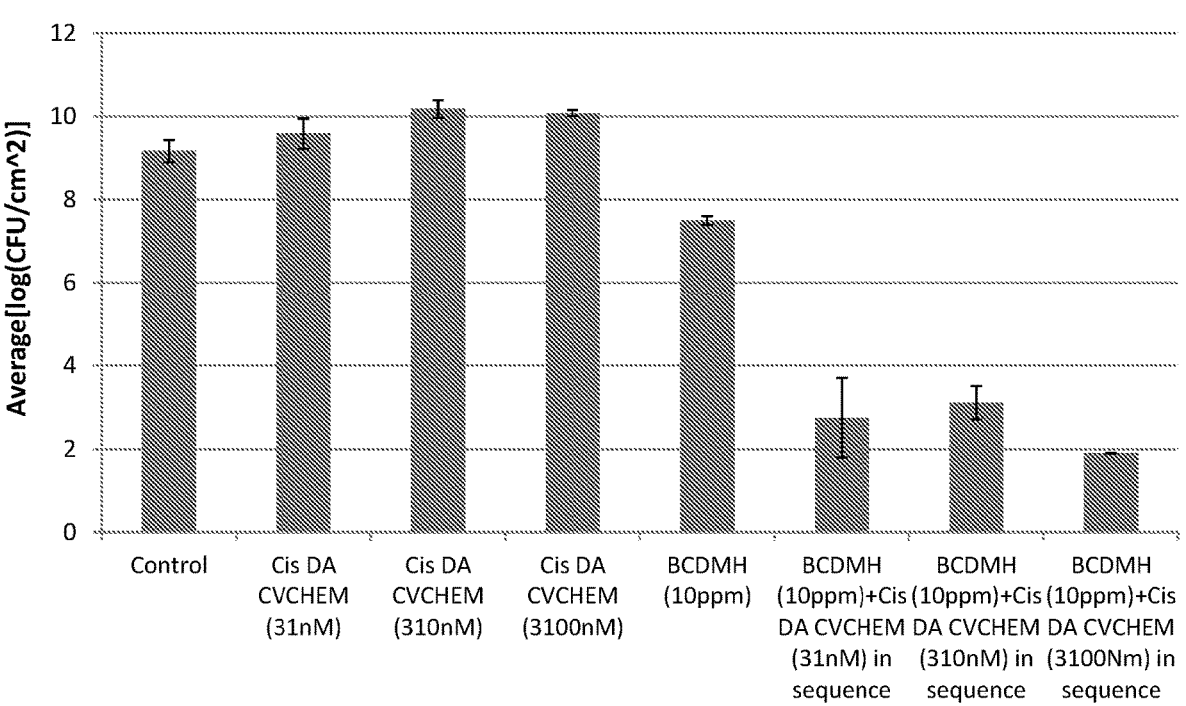

H. The effect of 10 ppm BCDMH on biofilms produced as described above, alone and in combination with different concentrations (31 nM, 310 nM and 3100 nM) of commercial CDA (CV-CHEM, 97% by GC) is illustrated in the bar diagram of FIG. 13. It is seen that CDA alone at all tested concentrations exhibits no useful effect compared to the control. The application of BCDMH alone reduces the biofilm. Notably, an enhancement of 4.5 log units was achieved by the combined treatment of CDA (31 nM and 310 nM) and of 5.5 log units (3100 nM) compared to the treatment with BCDMH alone (the combined treatment consists of addition of BCDMH to a sample that was in contact with CDA for one hour prior to the addition of the biocide).

Example 3

Reducing Dosage Levels of Bromine-Based Biocides with the Aid of CDA

The goal of the study was to estimate to which extent the addition of CDA can offset a decrease of the dosage level of the bromine-based biocide. That is, to offer combined bromine/CDA treatment program that is equally effective as currently acceptable, high-dosage level, acting-alone bromine.

The biocide tested was BCDMH. CDA of commercial source, 97% purity grade, was used. The experimental protocol of Example 2 was repeated (i.e., sequential treatment, CDA followed by BCDMH, applied to biofilm grown for three days, 1 hour biocide contact time).

Figure 14:
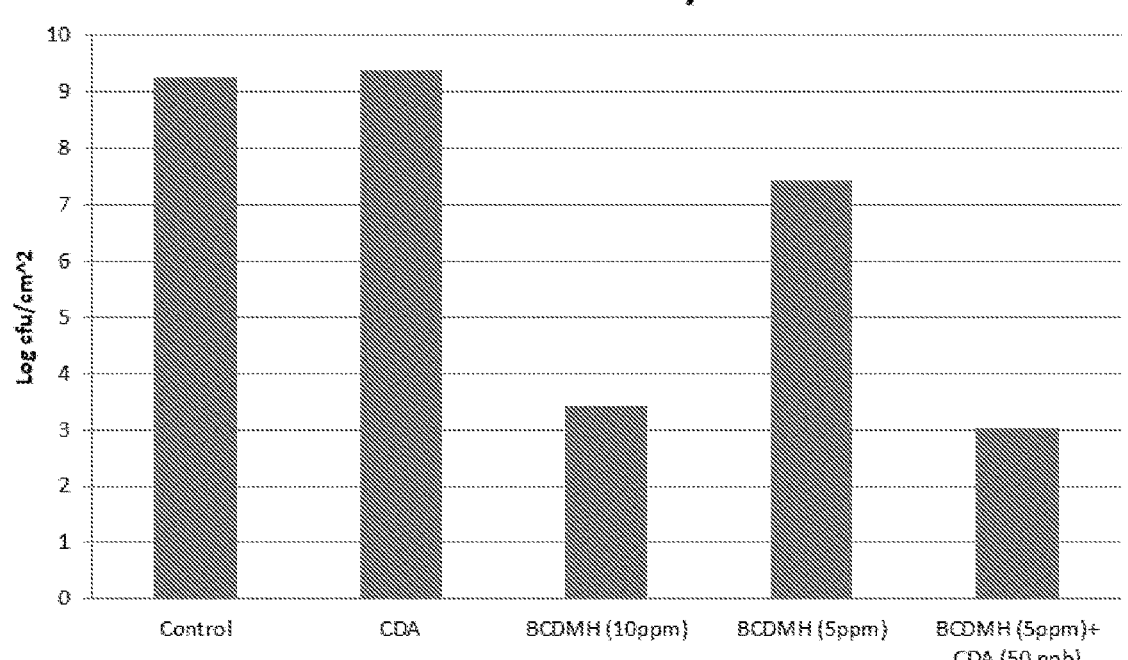

The results are presented in the form of a bar diagram in FIG. 14, showing that the effect of 5.0 ppm of BCDMH in the presence of 310 nM CDA is comparable to that of 10 ppm BCDMH in the absence of CDA. Hence, addition of very small amount of CDA to the water can offset a 50% decrease in the dosage level of the biocide.

Example 4

Reducing Dosage Levels of Bromine-Based Biocides with the Aid of CDA

CDA (commercial 97% purity grade) was applied in combination with varying quantities of bromine-based biocide (the dosage level of the biocide was varied in the range from 0 to 10 ppm) to investigate the ability of CDA to support the action of the biocide across a wide biocide concentration range. CDA was used at a constant concentration of 310 nM. The combined treatment bromine/CDA was compared to the solely applied bromine-based biocide.

The biocide tested was bromourea. The experimental protocol of Example 2 was repeated (i.e., sequential treatment, CDA followed by bromourea, applied to biofilm grown for three days, 1 hour biocide contact time).

Figure 15A:
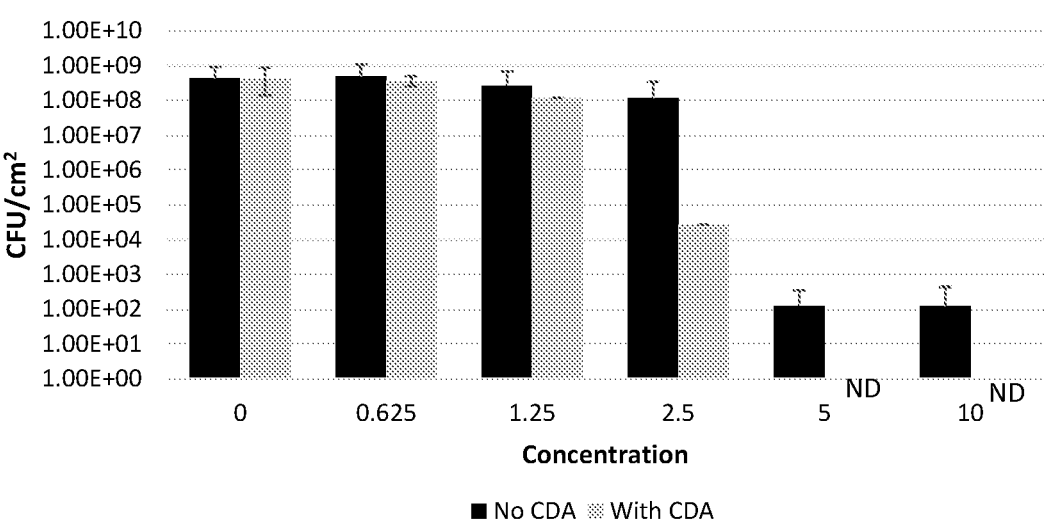
Figure 15B:
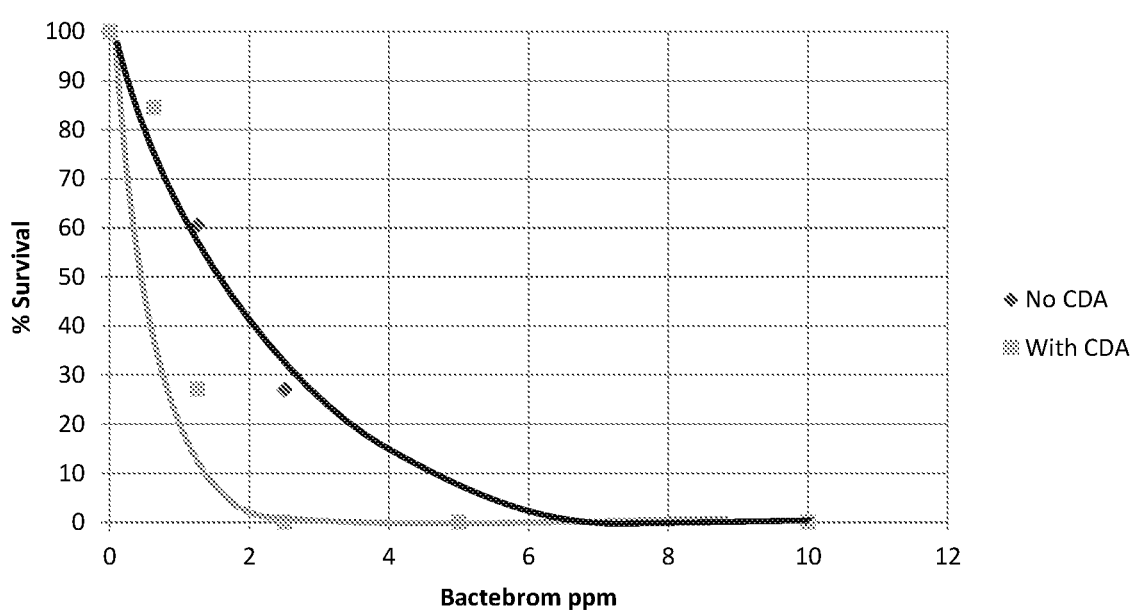

The results are shown in FIGS. 15A and 15B, in the form of survival plots corresponding to the solely applied biocide (marked by rhombuses) and the combined biocide/CDA treatment. The concentrations of the biocide tested were 0.0, 0.625, 1.25, 2.5, 5 and 10 ppm. The results indicate the effectiveness of the combined treatment against 3-day biofilm over the entire biocide concentration range (i.e., >0.5 ppm), demonstrating $LC_{50}$ (biofilm concentration at which 50% of the culture is killed) biofilm control at treatment level of 2.5 ppm bromourea/310 nM CDA and biofilm eradication concentration as low as 5 ppm bromourea/310 nM CDA.

Example 5

Enhancing the Effect of Bromine-Based Biocide on Planktonic Bacteria with the Aid of CDA (Sequential Application)

310 nM CDA and bromine-containing biocide were introduced into a mix of planktonic bacteria in a medium containing different levels of organic loading (TOC 10-3000 ppm). High organic loading tends to reduce the efficacy of antimicrobial agents in industrial applications and, therefore, the test was aimed to mimic these conditions. The test was performed in accordance with the modified European standard EN 1040: 2005: "Chemical disinfectants and antiseptics—Quantitative suspension test for the evaluation of basic bactericidal activity of chemical disinfectants and antiseptics—Tests method and requirements (phase 1)". 19 ml of phosphate buffer solution (pH=7) including tryptone in order to obtain a solution of TOC=30 ppm, and 1 ml of the tested bacteria suspension (consisted of *E. Coli* (ATCC 11229), *S. aureus* (ATCC 6538), *Enterobacter aerogenes*

(ATCC 130489) and *P. aeruginosa* (ATCC 13388)), at a concentration of $1.5 \times 10^8$-$5 \times 10^8$ CFU/ml, were placed into a container of suitable capacity. A stopwatch was started immediately and the container was placed in a water bath controlled at 30° C.

The activity was determined with 2.5 ppm BCDMH alone for a contact time of 3 hours. The combination of CDA (CV-CHEM) with 2.5 ppm BCDMH was tested when added in sequence (1 hour with CDA then additional 3 hours with BCDMH). At the desired contact time, 1 ml of the tested mixture was pipetted into a tube containing 9.0 ml neutralizer. Immediately after 5 sec of neutralization time, a sample of 1 ml was taken in duplicate and transferred to a Petri dish. TSA, cooled to 45±1° C., was added. The plates were incubated at 37±2° C. for 48 hours. Countable plates were counted and the number of colony-forming units was determined, for each plate.

Figure 16:
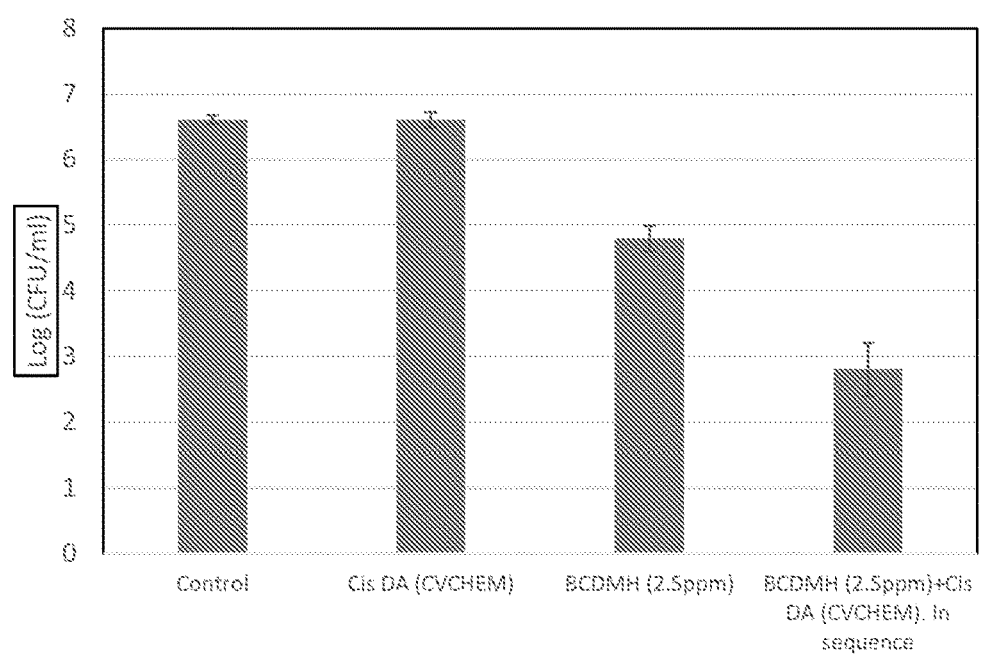

The results are presented in FIG. 16. As can be seen, enhancement of 2 log units was obtained when CDA (CV-CHEM) and BCDMH (2.5 ppm) were introduced in sequence compared with the effect achieved by BCDMH in the absence of CDA.

Example 6

Room Temperature Storage-Stable Composition of DENPA and CDA 22 mg of cis-2-decenoic acid (CiVentiChem, 96.72% purity) were charged into 50 ml flask, equipped with a stirrer 3.99 gr of C-103 (ICL, batch 640160147) were added, followed by 9.97 gr of PEG200 (Merck 8.07483.5000 Lot 56904983 451), 5.95 gr of DI water and 22 mg of BHT (Aldrich B1378-100G, BCBH9491V). The obtained solution was stirred till complete clarification; sonication at +30° C. is recommended if some particles are observed. Clear colorless solution of a total 30 gr and 20:50:30:0.1:0.1 weight ratio of C103-PEG$_{200}$-H$_2$O-CDA-BHT was obtained.

The solution was tested to determine the stability of the biocide and CDA and under storage at 25° C. over a two-month period. Neither DBNPA nor CDA underwent degradation in the 25° C./two-month test (analysis by HPLC).

Example 7

Room Temperature Storage-Stable Composition of Bronopol and CDA 47.6 mg or cis-2-decenoic acid (CiVentiChem, 96.72% purity) were charged into 50 ml flask, equipped with a stirrer. 9.01 gr of Bronopol (ICL, batch 17101607) were added, followed by 18.03 gr of propylene glycol (Biolab 16200201 Lot 1007861), 3.0 gr of DI water and 31.2 mg of BHT (Aldrich B1378-100G, BCBH9491V). After stirring for several minutes, undissolved traces of BHT were filtered through filtering paper for BHT particle removal. Clear colorless solution of a total 30 gr and 30:60:10:0.158:0.1 weight ratio of Bronopol-PG-H$_2$O-CDA-BHT was obtained.

The solution was tested to determine the stability of the biocide and CDA and under storage at 25° C. over a two-month period. Neither bronopol nor CDA underwent degradation in the 25° C./two-month test (analysis by HPLC).

Example 8

Bromine/CDA Versus Chlorine/CDA Effect on Biofilm

The purpose of the set of experiments reported in this Example was to check if the addition of CDA to bromine- and chlorine-based treatments generate comparable effects on the targeted biofilm. That is, whether CDA augments the action of bromine and chlorine on biofilm in equally effective manner. Sodium hypochlorite and BCDMH were chosen as illustrative chlorine and bromine biocides, respectively.

CDA of commercial source, 97% purity grade, was used. The experimental protocol of Example 2 was repeated (i.e., sequential treatment, CDA followed by the halogenated biocide, applied to biofilm grown for three days, 1 hour biocide contact time).

Figure 17:
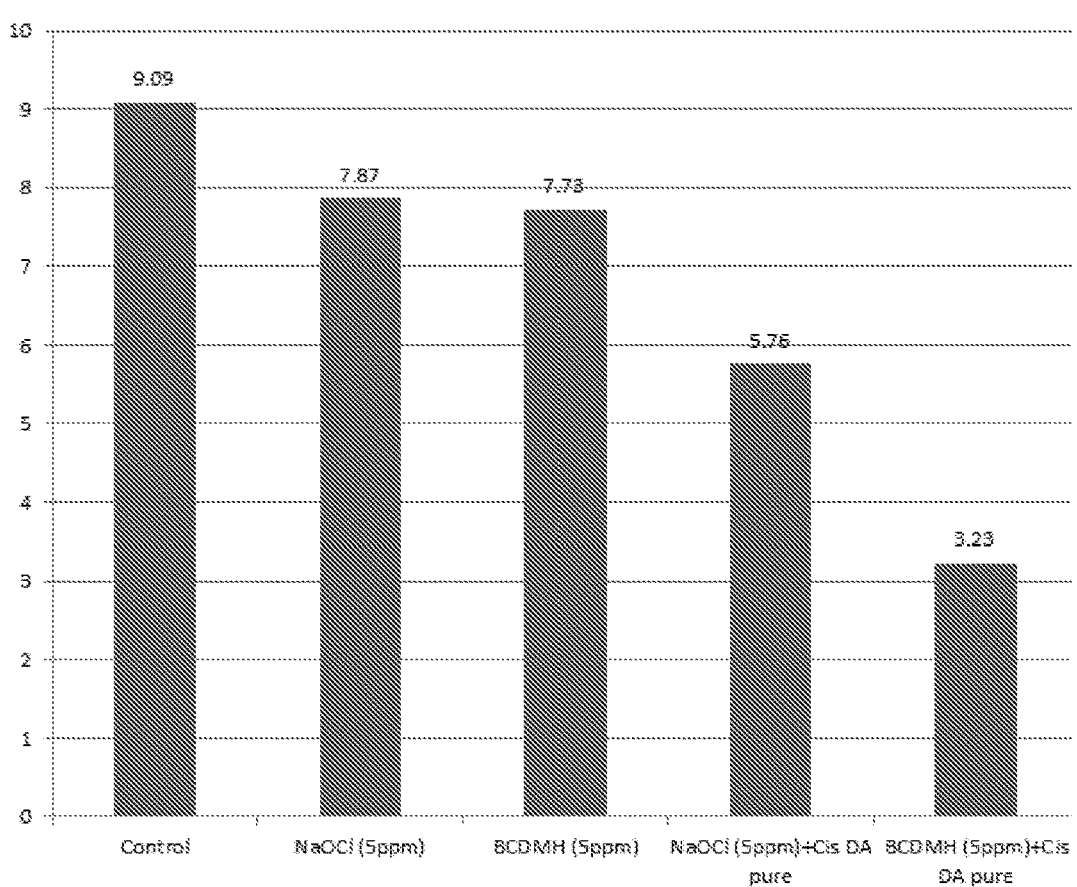

The bar diagram of FIG. 17 shows that sodium hypochlorite and BCDMH applied alone at dosage level of 5 ppm have comparable effect on biofilm. However, a surprisingly better effect was generated by the bromine/CDA combination of the invention on biofilm, compared with chlorine/CDA. The combination BCDMH/CDA applied at treatment level of 5 ppm BCDMH/310 nM CDA achieved 4.5 log units reduction versus the solely applied BCDMH treatment, whereas the corresponding hypochlorite/CDA treatment was able to improve to a lesser extent (2 log units reduction).

Example 9

Enhancing the Effect of Bromine-Based Biocide on Massive Biofilm with the Aid of CDA (Sequential Application)

The effect of the sequential addition of CDA and bromine-containing biocide was studied using *P. aeruginosa* biofilm grown in the drip flow tubes (according to a modification of standard ASTM 2647-13, standard Test Method for Quantification of *Pseudomonas aeruginosa* Biofilm Grown Using Drip Flow Biofilm Reactor with Low Shear and Continuous Flow). This method produces massive biofilm resulting with harsh conditions that are very difficult to treat. The addition of the bromine-containing biocide took place 120 min after the addition of 310 nM CDA (the biocide that was tested in this study was DBNPA).

Experimental Procedure a) A continuous once-through tube system was configured by using silicone coated latex tubes, connected to a peristaltic pump via additional silicone tubing.

b) The silicone coated latex tubes were inoculated by syringe injection of overnight cultures of *P. aeruginosa* (ATCC 700888), $5 \times 10^7$ CFU/ML in 10% TSB (Tryptic Soy Broth). The bacterial cells were allowed to attach (static incubation) to the tubing for 2 h (batch phase).

c) After 2 hours the system was moved into an incubator at 25° C. and a growth medium (10% TSB) was pumped at a flow rate of 10 mL/hr for ~42 hours.

d) Sequential addition of CDA and bromine-containing biocide: The biofilm treatment was done by exchanging the medium with buffered water (control) or buffered CDA solution and then exchanging to a biocide solution.

The following treatments were conducted:

1. Phosphate buffer for 5 hours (control)
2. Phosphate buffer for 2 hours followed by biocide solution (at different concentrations) for another 3 hours.
3. CDA buffer solution for 2 hours followed by biocide solution (at different concentrations) or buffer solution for another 3 hours (control).

e) After the end of the experiment, the silicone coated latex tubes were disconnected from the tubing and the biofilm was removed from within the tubes by inserting a specially made cleaning rod.

f) The biofilm was removed into a vial and disaggregated by vortex.

g) The sample was serially diluted. Each dilution was cultured in duplicate (on R2A agar) for colony growth using the pour plating method.

h) The plates were incubated at 36° C. for 17-20 h.

i) The appropriate number of colonies were counted.

Results

Figure 18:
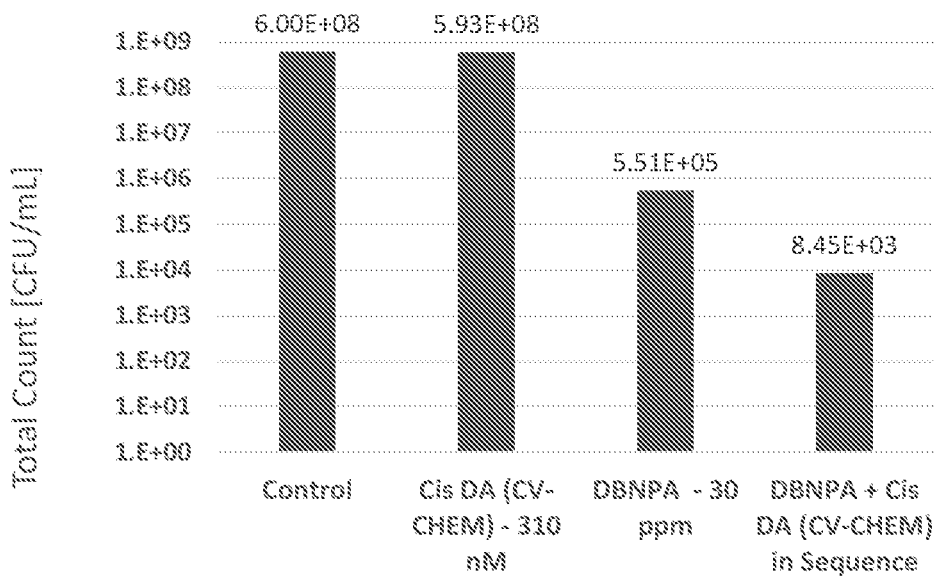

The results presented in FIG. 18 show that the effect of 30.0 ppm of DBNPA in the combined treatment of 310 nM CDA enhanced the biocidal effect of the biocide alone by ca 2 log orders.

Example 10

Enhancing the Effect of Bromine-Based Biocide on 3-Day Biofilm with the Aid of the Salt Form of CDA (Simultaneous Application)

Experimental stepwise acidification of CDA sodium/lithium salt indicates that cis-DA pKa value is in the range of 6.5-7.5. In several industrial applications the pH values of the treated water have higher alkalinity and therefore will promote the formation of the salt form of cis-DA. The effect of the simultaneous addition of CDA in its salt form and bromine-containing biocide was studied using *P. aeruginosa* biofilm grown in the CDC biofilm reactor on borosilicate glass coupons (test method E2562). The bromine-containing biocide tested was sulfamate-stabilized bromine (Bromosol), added simultaneously with 310 nM CDA for 60 min. The pH of the treated solution was in the range of pH 8-9—conditions which promote the formation of the salt of cis-DA.

Experimental Procedure

The efficacy test on the coupons was performed according to the single tube method (E2871-13). This test method is used for growing a reproducible *P. aeruginosa* biofilm in a CDC Biofilm Reactor.

Biofilm Formation:

The biofilm was established by operating the reactor in batch mode (no flow of the nutrients) for 4 h. A steady state population was reached after the reactor operated for an additional 3 days with continuous flow of the nutrients. During the entire 3-day period, the biofilm was exposed to continuous fluid shear from the rotation of a baffled stir bar. At the end of the 3 days, the biofilm from the coupons was sampled as follows:

a. The coupons were rinsed to remove planktonic cells. The rods were oriented in a vertical position directly over a 50 mL conical centrifuge tube that contained 30 mL sterile buffered water. The rods were immersed with a continuous motion into the buffered water with minimal to no splashing, then immediately removed. A new 50 mL conical tube containing 30 mL sterile buffered water was used for each rod.

b. The rods were held with one of the randomly selected coupons centered over an empty, sterile 50 mL conical tube. The set screws were loosened, allowing the coupons to drop directly to the bottom of the tube.

Simultaneous addition of CDA and bromine-containing biocide:

a. Four mL of a solution containing either phosphate buffer (untreated control), a buffer with 310 nM CDA or a buffer with different concentrations of biocides were slowly pipetted into the tubes containing the coupons.

b. Each tube was tapped to release any air bubbles trapped below the coupon.

c. The tubes (containing the control, CDA or the biocide) were incubated at 20° C., under shaking at 200 rpm for one-hour contact time.

d. After one-hour contact time, 36 ml of a neutralizer was added to each tube.

e. The combined treatment was carried out as a simultaneous treatment in which CDA (310 nM CDA) and the biocide were added together to the tubes. The tubes were incubated at 20° C., under shaking at 200 rpm for one-hour contact time. The pH measured in the system was between 8 to 9.

After the one-hour contact time, 36 ml of a neutralizer was added to each tube.

Removing and Disaggregating the Biofilm:

a. Each tube was vortexed using Vortex Genie-2 Model no. G560E on the highest setting for 30 s.

b. The tubes were sonicated at 45 kHz for 30 s.

c. The tubes were vortexed as described above, then sonicated and vortexed again.

d. The samples were serially diluted in buffered water.

e. Each dilution was cultured in duplicate (on R2A agar) for colony growth using the pour plating method.

f. The plates were incubated at 35° C. for 72 h.

g. The appropriate number of colonies were counted.

Figure 19:
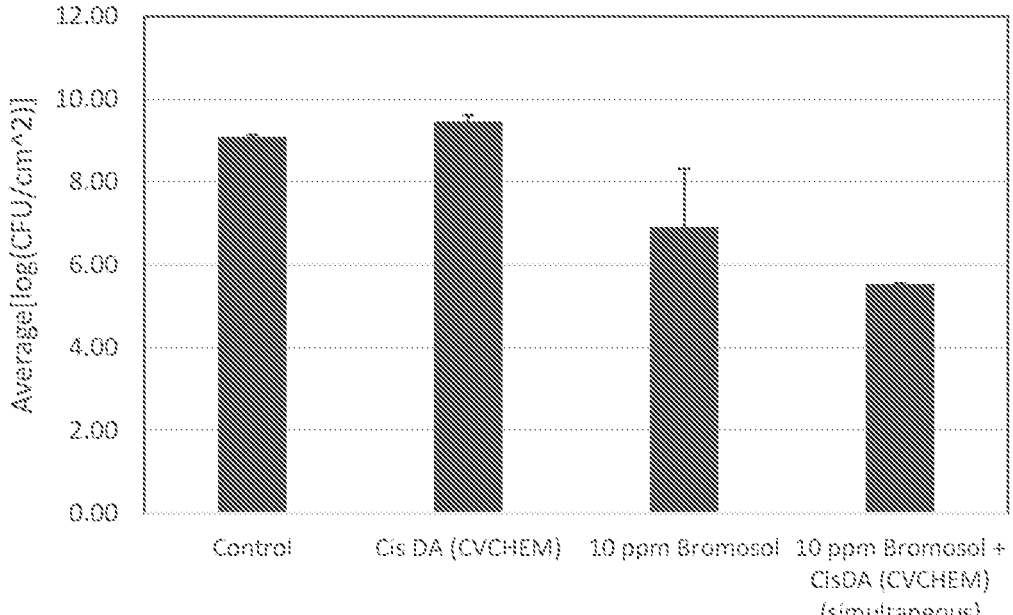

Results:

The effect of 10 ppm sulfamate-stabilized bromine (Bromosol) on biofilms produced as described above, alone and in combination with 310 nM CDA is illustrated in the bar diagram of FIG. 19. It is seen that CDA alone exhibits no useful effect compared to the control. The application of Bromosol alone reduces the biofilm (2.5 log units). The combined treatment (that is, CDA with the biocide) achieves a further biofilm reduction compared to the treatment with the biocide alone, enhancement of 1.4 log units.

The invention claimed is:

1. A method of microbial control in water comprising adding to the water one or more bromine-based biocide(s) and cis-2-decenoic acid (CDA) or a salt thereof, wherein the CDA is low purity CDA grade of 50-95% purity as measured by gas chromatography.

2. The method according to claim 1, wherein the microbial control comprises combatting planktonic bacteria and/or biofilm bacteria on a surface in contact with the water and/or inhibiting biofilm formation on a surface prone to biofilm growth.

3. The method according to claim 1, wherein the one or more bromine-based biocide(s) comprises a non-oxidizing bromine-based biocide.

4. The method according to claim 3, wherein the non-oxidizing bromine-based biocide is selected from the group consisting of: 2-bromo-2-nitro-1,3-propanediol (Bronopol); and 2,2-dibromo-3-nitrilopropionamide (DBNPA).

5. The method according to claim 1, wherein the one or more bromine-based biocide(s) comprises an oxidizing bromine-based biocide.

6. The method according to claim 5, wherein the oxidizing bromine-based biocide is 1,3-dihalo-5,5-dialkylhydantoin, wherein at least one of the halogen atoms is bromine, and the alkyl groups may be the same or different.

7. The method according to claim 6, wherein the 1,3-dihalo-5,5-dialkylhydantoin is selected from the group consisting of 1-bromo-3-chloro-5,5-dimethylhydantoin, 1-chloro-3-bromo-5,5-dimethylhydantoin, 1,3-dibromo-5,5-dimethylhydantoin and 1-bromo-3-chloro-methylethyl-hydantoin, or mixtures thereof.

8. The method according to claim 5, wherein the oxidizing bromine-based biocide is an on-site oxidized bromide source, which releases active bromine species in water.

9. The method according to claim 8, wherein the on-site oxidized bromide source is selected from the group consisting of:

sodium bromide, which is oxidized on-site with hypochlorite, chlorine or electrochemically to produce its active form, to be added to a water system to be treated;

HBr, which is oxidized on-site with hypochlorite, chlorine or electrochemically to produce its active form, to be added to the water system to be treated;

ammonium bromide, which is oxidized on-site with hypochlorite, chlorine or electrochemically to produce its active form, to be added to the water system to be treated; and a solution of HBr and urea, which reacts with hypochlorite, chlorine or electrochemically on-site to produce the bromourea active form, to be added to the water system to be treated.

10. The method according to claim 1, wherein an effective microbiocidal dosage of the one or more bromine-based biocide(s) is from 1 to 100 ppm and an enhancement-inducing amount of the cis-2-decenoic acid is from 0.005 to 5 ppm.

11. The method according to claim 1, wherein the one or more bromine-based biocide(s) and the CDA are supplied to an industrial water stream in contact with an infested surface using multiple feed solutions, whereby the one or more bromine-based biocide(s) and the CDA are added sequentially or simultaneously to the water.

12. The method according to claim 1, wherein the one or more bromine-based biocide(s) and the CDA are supplied to an industrial water stream in contact with an infested surface using a single feed solution, whereby the one or more bromine-based biocide(s) and the CDA are added simultaneously to the water.

13. The method according to claim 12, wherein the one or more bromine-based biocide(s) comprises a non-oxidizing biocide, and wherein the one or more bromine-based biocide (s) and the CDA are formulated in a liquid concentrate supplied to the industrial water stream using the single feed solution.

14. The method according to claim 1, comprising combatting biofilm bacteria by adding to the water an effective microbiocidal dosage of the one or more bromine-based biocide(s) and an enhancement-inducing amount of the cis-2-decenoic acid to achieve enhancement of at least 2 log units in biofilm reduction compared with the same dosage of the biocide acting alone.

15. The method according to claim 9, wherein the on-site oxidized bromide source is sodium bromide, which is oxidized on-site with hypochlorite, chlorine or electrochemically to produce its active form, to be added to the water system to be treated.

16. The method according to claim 9, wherein the on-site oxidized bromide source is HBr, which is oxidized on-site with hypochlorite, chlorine or electrochemically to produce its active form, to be added to the water system to be treated.

17. The method according to claim 9, wherein the on-site oxidized bromide source is ammonium bromide, which is oxidized on-site with hypochlorite, chlorine or electrochemically to produce its active form, to be added to the water system to be treated.

18. The method according to claim 9, wherein the on-site oxidized bromide source is a solution of HBr and urea, which reacts with hypochlorite, chlorine or electrochemically on-site to produce the bromourea active form, to be added to the water system to be treated.

19. The method according to claim 10, wherein the enhancement-inducing amount of cis-2-decenoic acid is from 0.005 to 0.5 ppm.

* * * * *